(12) United States Patent
Bondinell et al.

(10) Patent No.: US 6,399,656 B1
(45) Date of Patent: Jun. 4, 2002

(54) COMPOUNDS AND METHODS

(75) Inventors: William E Bondinell, Wayne; Thomas W Ku, Dresher; Michael J Neeb, Berwyn, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/744,629

(22) PCT Filed: Jul. 28, 1999

(86) PCT No.: PCT/US99/17118
§ 371 (c)(1),
(2), (4) Date: Apr. 9, 2001

(87) PCT Pub. No.: WO00/06085
PCT Pub. Date: Feb. 10, 2000

Related U.S. Application Data

(60) Provisional application No. 60/094,424, filed on Apr. 28, 1998, and provisional application No. 60/094,414, filed on Jul. 28, 1998.

(51) Int. Cl.$^7$ .................... A61K 31/352; C07D 311/04
(52) U.S. Cl. ....................................... 514/456; 549/405
(58) Field of Search .......................... 514/456; 549/405

(56) References Cited

U.S. PATENT DOCUMENTS 4,000,143 A   12/1976  Dykstra et al. ........ 260/293.67

FOREIGN PATENT DOCUMENTS

| WO | WO 95/04729 | 2/1995 |
| WO | WO 95/06637 | 3/1995 |
| WO | WO 95/06644 | 3/1995 |

*Primary Examiner*—Phyllis G. Spivack
(74) *Attorney, Agent, or Firm*—Nora Stein-Fernandez; Stephen A. Venetianer; Charles M. Kinzig

(57) ABSTRACT

This invention relates to substituted heteroanilide compounds which are modulators, agonists or antagonists, of the CCR5 receptior. In addition, this invention relates to the treatment and prevention of disease states mediatd by CCR5.

5 Claims, No Drawings

COMPOUNDS AND METHODS

This is a 371 of International Application PCT/US99/17118 filed Jul. 28, 1999 which claims benefit from the following Provisional Applications Ser. No. 60/094,424 and Ser. No. 60/094,414 filed Jul. 28, 1998.

FIELD OF THE INVENTION

This invention relates to substituted heteroanilide compounds which are modulators, agonists or antagonists, of the CC chemokine receptor CC-CKR5 now designated as CCR5 (*Nature Medicine* 1996, 2, 1174–8). In addition, this invention relates to the treatment and prevention of disease states mediated by CCR5.

BACKGROUND OF THE INVENTION

T cells are not only key regulators of the immune response to infectious agents but are believed critical for the initiation and maintenance of the inflammatory reaction in a variety of chronic diseases. Increased numbers or enhanced activation state of T cells, especially CD4+ T cells, have been demonstrated in the synovium of individuals with rheumatoid arthritis (M. J. Elliott and R. N. Maini, *Int. Arch. Allergy Immunol.* 104: 112–1125, 1994), in the bronchial mucosa of asthmatics (C. J. Cofrigan and A. B. Kay, *Immunol. Today* 13:501–506, 1992), in the lesions of multiple sclerosis (R. Martin and H. F. McFarland, *Crit. Rev. Clin. Lab. Sci.* 32: 121–1827 1995), in psoriatic lesions (J. L. Jones, J. Berth-Jone, A. Fletcher and P. E. Hutchinson, *J. Pathol.* 174: 77–82, 1994) and in the fatty streaks of atherosclerosis (R. Ross, *Annu. Rev. Physiol.* 57: 791–804, 1995).

T cells, as well as other inflammatory cells, will migrate into tissues in response to the production of a variety of chemotactic factors. Among these factors are a superfamily of 8–12 kDa proteins known as the chemokines. These proteins share structural features such as the presence of 3–4 conserved cysteine residues. RANTES, which stands for Regulated upon Activation Normal T cell Expressed and Secreted, is an 8 kDa protein member of CC branch of the chemokine family. These proteins recruit and activate immune and inflammatory cells through an interaction with G-protein coupled receptors. The CC branch is defined by the absence of an intervening amino acid residue between the first two cysteine residues and members of this family predominately elicit the migration of mononuclear cells, eosinophils and basophils (M. Baggiolini, B. Dewald, and B. Moser, *Adv. Immunol.* 55: 97–179, 1994: and J. J. Oppenheim, C. O. C. Zachariae, N. Mukaida and K. Matsushima, *Annu. Rev. Immunol.* 9: 617–648, 1991).

RANTES potently produces chemotaxis of T cells, basophils, eosinophils, monocytes and mast cells. RANTES was originally identified as gene product induced late after antigen activation of T-cells (T. J. Schall, J. Jongstra, B. J. Dyer, J. Jorgensen, et al., *J. Immunol.* 141:1018–1025, 1988), however, RANTES has been shown to be synthesized and secreted by a diverse group of cells that include epithelial and endothelial cells (C. Stellato, L. A. Beck. G. A. Gorgone, D. Proud, et al., *J. Immunol.* 155: 410–418, 1995; and A. Marfaing-Koka, O. Devergne, G. Gorgone, A. Portier, et al., *J. Immunol.* 154: 1870–1878, 1994), synovial fibroblasts (P. Rathanaswami, M. Hachicha, M. Sadick. T. J. Schall. et al., *J. Biol. Chem.* 268: 5834–5839, 1993) and dermal fibroblasts (M. Sticherling, M. Kupper, F. Koltrowitz, E. Bornscheuer, et al., *J. Invest. Dermatol.* 105: 585–591, 1995), mesangial cells (G. Wolf, S. Aberle. F. Thaiss, et al., *Kidney Int.* 44: 795–804, 1994) and platelets (Y. Koameyoshi, A. Dorschner, A. I. Mallet, E. Christophers, et al., *J. Exp. Med.* 176: 587–592, 1992). In these cells RANTES mRNA is rapidly upregulated in response to IL-1 or TNFa. Although RANTES mRNA is not usually detected in normal tissues (J. M. Pattison, P. J. Nelson, and A. M. Krensky. Clin. Immunother. 4: 1–8, 1995), increased mRNA or protein has been found in diseases characterized by a mononuclear infiltrate. For example, RANTES mRNA was visualized using in situ hybridization in renal allografts undergoing rejection (J. M. Pattison, P. J. Nelson, and A. M. Krensky, *Clin. Immunother.* 4: 1–8, 1995; and K. C. Nadeau, H. Azuma and N. I. Tilney. *Proc. Natl. Acad. USA* 92: 8729–8733, 1995) in the skin of atopic dermatitis patients after exposure to antigen (S. Ying, L. Taborda-Barata, Q. Meng, M. Humbert, et al., *J. Exp. Med.* 181: 2153–2159, 1995), and in endothelial cells of coronary arteries undergoing accelerated atherosclerosis after cardiac transplant (J. M. Pattison, P. J. Nelson, and A. M. Krensky, *Clin. Immunother.* 4: 1–8, 1995). Further, increased immunoreactive protein for RANTES has been detected in bronchoalveolar lavage fluid (R. Alam, J. York, M. Boyers, et al.,*Am. J. Resp. Crit. Care Med.* 149: A951, 1994) and sputum from asthmatic individuals (C. M. Gelder, P. S. Thomas, D. H. Yates, I. M. Adcock, et al., *Thorax* 50: 1033–1037, 1995).

Several receptors have been identified that bind RANTES. In particular, CCR5, when expressed in either HEK 293 cells or CHO cells, binds RANTES. This receptor is expressed in T-cells and in monocytes and macrophages, immune/inflammatory cells which are important in the maintenance of a chronic inflammatory reaction. Pharmacological characterization of CCR5 indicates similarities to the RANTES binding site observed on isolated T cells. Therefore, antagonism of RANTES' action on CCR5, as well as antagonism of other natural modulators of CCR5, should inhibit the recruitment and activation of T cells and macrophages into inflammatory lesions and provide a novel therapeutic approach for the treatment of atopic and autoimmune disorders.

Since T cells express CCR5, selective receptor modulators of CCR5, particularly antagonists, are likely to provide beneficial effects in diseases including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, preferably humans. Furthermore, since CD8+ T cells have been implicated in COPD, CCR5 may play a role in their recruitment and therefore antagonists to CCR5 could provide potential therapeutic in the treatment of COPD. Also, since CCR5 is a co-receptor for the entry of HIV into cells, selective receptor modulators may be useful in the treatment of HIV infection.

Surprisingly, it has now been discovered that this class of non-peptide compounds, in particular substituted heteroanilide compounds of this invention, function as CCR5 receptor modulators, and therefore, have utility in the treatment and prevention of disease states mediated by CCR5 receptor mechanisms.

SUMMARY OF THE INVENTION

In one aspect, the present invention is to novel compounds of formula (I), or pharmaceutically active salts thereof, and their novel use in treating the above-mentioned CCR5-mediated disease states:

Ar-L-E                                    Formula I in which Ar represents a group of Formula (i) or (ii):

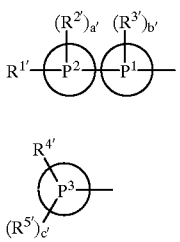

(i)

(ii)

wherein:
the basic nitrogen in moiety E may be optionally quaternized with $C_{1-6}$alkyl or is optionally present as the N-oxide;

$P^1$ and $P^2$ are independently phenyl, fused bicyclic aryl, a monocyclic heterocyclic ring of 5- to 7-members containing 1 to 3 heteroatoms selected from oxygen, nitrogen and sulfur, or a fused bicyclic heterocyclic ring of 8 to 11-members containing 1 to 3 heteroatoms selected from oxygen, nitrogen or sulfur, providing that at least one of $P^1$ and $P^2$ is a heterocyclic group;

$P^3$ is a monocyclic heterocyclic ring of 5- to 7-members containing 1 to 3 heteroatoms selected from oxygen, nitrogen and sulfur, or a fused bicyclic heterocyclic ring of 8 to 11-members containing 1 to 3 heteroatoms selected from oxygen, nitrogen or sulfur;

L is a group of formula —C(=V)—DR$^{6'}$—, —DR$^{7'}$—C(=V)—, —CH$_2$NH—, or —NHCH$_2$—;

V is oxygen or sulfur;

D is nitrogen, carbon, or a CH group, $R^{1'}$, $R^{2'}$, and $R^{4'}$ are independently hydrogen, $C_{1-6}$alkyl, $C_{2-6}$alkenyl, $C_{2-6}$alkynyl, $C_{3-7}$cycloalkyl, $C_{3-7}$cycloalkenyl, aryl, $(CH_2)_{d'}NR^{8'}R^{9'}$, $(CH_2)_{d'}NR^{8'}COR^{10'}$, $(CH_2)_{d'}NR^{8'}CO_2R^{11'}$, $(CH_2)_{d'}NR^{8'}SO_2R^{12'}$, $(CH_2)_{d'}CONR^{13'}R^{14'}$, hydroxyC$_{1-6}$alkyl, $C_{1-4}$alkoxyalkyl (optionally substituted by a $C_{1-4}$alkoxy or hydroxy group), $(CH_2)_dCO_2C_{1-6}$alkyl, $(CH_2)_eOC(O)R^{15'}$, $CR^{16'}$=NOR$^{17'}$, CNR$^{18'}$=NOR$^{17'}$, COR$^{19'}$, CONR$^{13'}R^{14'}$, CONR$^{13}$(CH$_2$)$_fOC_{1-4}$alkyl. CONR$^{13'}$(CH$_2$)$_{d'}CO_2R^{20'}$. CONHNR$^{21'}R^{22'}$, CONR$^{13'}SO_2R^{23'}$, CO$_2R^{24'}$, cyano, trifluoromethyl, NR$^{8'}R^{9'}$, NR$^{8'}COR^{10'}$. NR$^{25'}CO(CH_2)_{d'}NR^{25'}R^{26'}$, NR$^{25'}CONR^{25'}R^{26'}$, NR$^{8'}CO_2R^{11'}$,NR$^{8'}SO_2R^{12'}$, N=CNR$^{25'}NR^{25'}R^{26'}$, nitro, hydroxy, $C_{1-6}$alkoxy, hydroxy $C_{1-6}$alkoxy, $C_{1-6}$alkoxyC$_{1-6}$alkoxy, OC(O)NR$^{27'}R^{28'}$, SR$^{29'}$, SOR$^{30'}$, SO$_2R^{30'}$. SO$_2NR^{31'}R^{32'}$, halogen, $C_{1-6}$alkanoyl, CO$_2$(CH$_2$)$_{d'}OR^{33'}$, or $R^{1'}$ is an optionally substituted 5 to 7-membered heterocyclic ring containing 1 to 4 heteroatoms selected from oxygen, nitrogen or sulfur, $R^{3'}$ and $R^{5'}$ are independently hydrogen, $C_{1-6}$alkyl, $C_{3-6}$cycloalkyl, $C_{3-6}$cycloalkenyl, hydroxyC$_{1-6}$alkyl, $C_{1-6}$alkylOC$_{1-6}$alkyl, CONR$^{34'}R^{35'}$, CO$_2R^{36'}$, cyano, aryl, trifluoromethyl, NR$^{37'}R^{38'}$, nitro, hydroxy, $C_{1-6}$alkoxy, $C_{1-6}$alkanoyl, acyloxy, or halogen;

$R^{16'}$, $R^{17'}$, $R^{18'}$, $R^{19'}$, $R^{20'}$, $R^{21'}$, $R^{22'}$, $R^{25'}$, $R^{26'}$, $R^{29'}$, $R^{33'}$, $R^{34'}$, $R^{35'}$, $R^{36'}$, $R^{37'}$, and $R^{38'}$ are independently hydrogen or $C_{1-6}$alkyl;

$R^{6'}$ is hydrogen or $C_{1-6}$alkyl, providing that D is nitrogen or a CH group;

$R^{7'}$ is hydrogen or $C_{1-6}$alkyl, providing that D is nitrogen or a CH group;

$R^{8'}$ and $R^{9'}$ are independently hydrogen or $C_{1-6}$alkyl, or $R^{8'}$ and $R^{9'}$ together with the nitrogen to which they are attached, forms a 5- to 6-membered heterocyclic ring, which may optionally be substituted by an oxo group, and when there are six members may optionally contain in the ring one oxygen or one sulfur atom;

$R^{10'}$ is hydrogen, $C_{1-6}$alkyl, or $C_{1-4}$alkoxyalkyl;

$R^{11'}$, $R^{23'}$, and $R^{30'}$ are independently $C_{1-6}$alkyl;

$R^{12'}$ is $C_{1-6}$alkyl or phenyl;

$R^{13'}$ and $R^{14'}$ are independently hydrogen or $C_{1-6}$alkyl, or $R^{13'}$ and $R^{14'}$ together with the nitrogen to which they are attached form a 5- to 6-membered saturated heterocyclic ring which when there are 6 ring members, may optionally contain in the ring one oxygen or one sulfur atom;

$R^{15'}$ is $C^{1-4}$alkyl, optionally substituted by $C_{1-6}$alkoxy;

$R^{24'}$ is hydrogen or $C_{1-6}$alkyl optionally substituted with one or two substituents selected from $C_{1-6}$alkyl, $C_{1-6}$alkoxy, hydroxy, or NR$^{8'}R^{9'}$;

$R^{27'}$ and $R^{28'}$ are independently hydrogen or $C_{1-6}$alkyl, or $R^{27'}$ and $R^{28'}$ together with the nitrogen to which they are attached form a 5- to 6-membered heterocyclic ring which, when there are six ring members, may optionally contain in the ring one oxygen or sulfur atom;

$R^{31'}$ and $R^{32'}$ are independently hydrogen or $C_{1-6}$alkyl, or $R^{31'}$ and $R^{32'}$ together with the nitrogen to which they are attached form 5- to 6-membered heterocyclic ring which, when there are six ring members, may optionally contain in the ring one oxygen or one sulfur atom;

a' and b' are independently 1,2, or 3;

c' is 0, 1, or 2;

d' is 1, 2, 3, or 4;

e' is 0, 1, 2, or 3;

f' is 1, 2, or 3;

E represents (a):

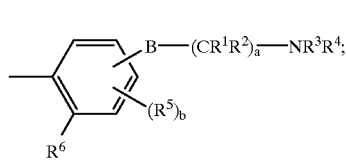

(a)

in which

B is oxygen, S(O)$_c$, CR$^7$=CR$^8$, or CR$^7R^8$, or B is NR$^9$;

$R^1$ and $R^2$ are independently hydrogen or $C_{1-6}$alkyl; alternatively B(CR$^1R^2$)$_a$ is OCR$^1R^2$CR$^1$(OH)CR$^1R^2$ or OCR$^1R^2$CR$^1$(OCOCH$_3$)CR$^1R^2$;

$R^3$ and $R^4$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring which may contain an additional heteroatom selected from oxygen, nitrogen or sulfur, where optional substituents include $C_{1-6}$alkyl, aryl, CONR$^{10}R^{11}$, NR$^{10}R^{11}$, hydroxy, OCOR$^{12}$, NHCOC$_{0-6}$alkyl where alkyl is optionally substituted by OH, NHCOCF$_3$, NHSO$_2R^{13}$, and NHCO$_2R^{14}$;

$R^5$ is hydrogen, $C_{1-6}$alkyl, aryl, CN, CONR$^{15}R^{16}$, CO$_2R^{17}$, trifluoromethyl, NHCO$_2R^{18}$, hydroxy, $C_{1-6}$alkoxy, benzyloxy, OCH$_2$CO$_2C_{1-6}$alkyl, OCF$_3$, S(O)$_dR^{19}$, SO$_2NR^{20}R^{21}$ or halogen;

$R^6$ is hydroge, $C_{1-6}$alkyl, aryl, trifluoromethyl, hydroxy, $C_{1-6}$alkoxy or halogen, or $R^6$ taken together with $R^{6'}$ forms a group D where D is $(CR^{22}R^{23})_e$ or D is $(CR^{22}R^{23})_f$-G where G is oxygen, sulfur or $CR^{22}$=$CR^{23}$, $CR^{22}$=N, =$CR^{22}$O, =$CR^{22}$S, or =$CR^{22}$-$NR^{23}$;

$R^7, R^8, R^{10}, R^{11}, R^{12}, R^{15}, R^{16}, R^{17}, R^{20}, R^{21}, R^{22}$, and $R^{23}$ are independently hydrogen or $C_{1-6}$alkyl;

$R^9$ is hydrogen, $C_{1-6}$alkyl, or phenyl$C_{1-6}$alkyl;

$R^{13}, R^{14}, R^{18}$, and $R^{19}$ are independently $C_{1-6}$alkyl;

a is 1, 2, 3, or 4;

b is 1 or 2;

c and d are independently 0, 1 or 2;

e is 2, 3 or 4, f is 0, 1, 2 or 3:

alternatively. E represents (b):

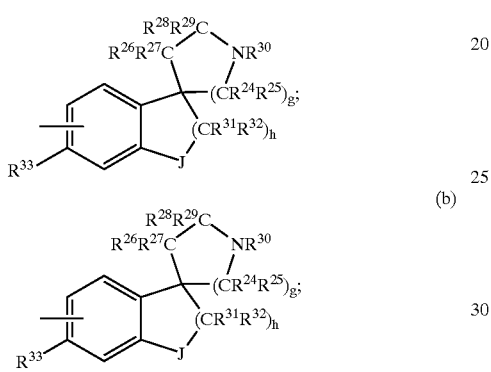

$R^{24}, R^{25}, R^{26}, R^{27}, R^{28}, R^{29}, R^{31}$, and $R^{32}$ are independently hydrogen or $C_{1-6}$alkyl;

$R^{30}$ is hydrogen, $C_{1-6}$alkyl, or $C_{3-7}$cycloalkyl;

$R^{33}$ is hydrogen, $C_{1-6}$alkyl, trifluoromethyl, hydroxy, or halogen, or $R^{33}$ and $R^{6'}$ together form a group —K— where K is $(CR^{34}R^{35})_i$ or K is $(CR^{34}R^{35})_j$-M and M is oxygen, sulfur, $CR^{34}$=$CR^{35}$, $CR^{34}$=N, or N=N:

J is oxygen, $CR^{36}R^{37}$, or $NR^{38}$, or J is a group $S(O)_k$ $R^{34}, R^{35}, R^{36}, R^{37}$, and $R^{38}$ are independently hydrogen or $C_{1-6}$alkyl;

g is 1, 2, or 3;

h is 1, 2 or 3;

i is 2, 3, or 4;

j is 0, 1, 2, or 3;

k is 0, 1 or 2;

alternatively, E represents (c):

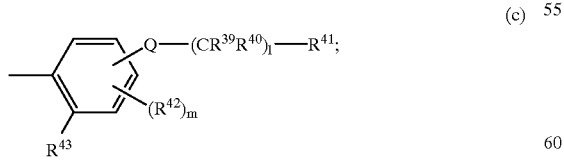

in which:

Q is oxygen, $S(O)_n$, $CR^{44}$=$CR^{45}$, $CR^{44}R^{45}$, or Q is $NR^{46}$;

$R^{39}$ and $R^{40}$ are independently hydrogen or $C_{1-6}$alkyl;

$R^{41}$ is a group of formula (d):

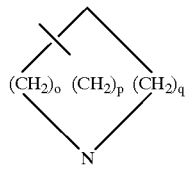

or $R^{41}$ is a group of formula (e):

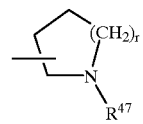

$R^{42}$ is hydrogen, $C_{1-6}$alkyl, aryl, CN, $CONR^{48}R^{49}$, $CO_2R^{50}$, trifluoromethyl, $NHCO_2R^{51}$, hydroxy, $C_{1-6}$alkoxy, benzyloxy, $OCH_2CO_2C_{1-6}$alkyl, $OCF_3$, $S(O)_sR^{52}$, $SO_2NR^{53}R^{54}$, or halogen;

$R^{43}$ is hydrogen or $R^{43}$ together with $R^{6'}$ forms a group R where R is $CR^{55}$=$CR^{56}$, $CR^{55}$=$CR^{56}CR^{55}R^{56}$, or $(CR^{55}R^{56})t$;

$R^{44}, R^{45}, R^{46}, R^{48}, R^{49}, R^{50}, R^{53}, R^{54}, R^{55}$, and $R^{56}$ are independently hydrogen or $C_{1-6}$alkyl;

$R^{47}$ is hydrogen, $C_{1-6}$alkyl, or $C_{3-7}$ cycloalkyl;

$R^{51}$ and $R^{52}$ are independently $C_{1-6}$alkyl;

l is 0, 1, 2, or 3;

m is 1 or 2;

n is 0, 1, or 2 o, p, and q are independently integers having the value 1, 2, or 3;

r is 0, 1, 2, or 3;

s is 0, 1, or 2;

t is 2 or 3;

alternatively, E represents (f):

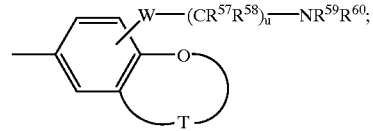

$R^{57}$ and $R^{58}$ are independently hydrogen or $C_{1-6}$alkyl;

$R^{59}$ and $R^{60}$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring which may contain an additional heteroatom selected from oxygen, nitrogen or sulfur, where optional substituents include $C_{1-6}$alkyl, aryl, $CONR^{61}R^{62}$, $NR^{61}R^{62}$, hydroxy, $OCOR^{63}$, $NHCOC_{0-6}$alkyl where alkyl is optionally substituted by OH, $NHCOCF_3$, $NHSO_2R^{64}$, and $NHCO_2R^{65}$;

T is —$(CR^{66}R^{67})_v$— or —$O(CR^{66}R^{67})_w$—;

W is oxygen, $S(O)_x$, $NR^{68}$, or W is $CR^{69}$=$CR^{70}$ or $CR^{69}R^{70}$;

$R^{61}, R^{62}, R^{63}, R^{66}, R^{67} R^{68}, R^{69}$, and $R^{70}$ are independently hydrogen or $C_{1-6}$alkyl;

$R^{64}$ and $R^{65}$ are independently $C_{1-6}$alkyl;

u is 1 to 4;

v is 2 or 3;
w is 1, 2, or 3;
x is 0, 1 or 2;
alternatively, E represents a group (g):

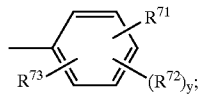

(g)

$R^{71}$ is an optionally substituted 5 to 7-membered saturated or partially saturated heterocyclic ring containing 1 to 3 heteroatoms selected from nitrogen, oxygen or sulfur or $R^{71}$ is an optionally substituted 6,6 or 6,5 bicyclic ring containing a nitrogen atom and optionally a further heteroatom selected from oxygen, nitrogen or sulfur;

$R^{72}$ is hydrogen, $C_{1-6}$alkyl, aryl, CN, $CONR^{74}R^{75}$, $CO_2R^{76}$, trifluoromethyl, $NHCO_2R^{77}$, hydroxy, $C_{1-6}$alkoxy, benzyloxy, $OCH_2CO_2C_{1-6}$alkyl, $OCF_3$, $S(O)_zR^{78}$, $SO_2NR^{79}R^{80}$, or halogen;

$R^{73}$ is hydrogen, $C_{1-6}$alkyl, hydroxy, $C_{1-6}$alkoxy or halogen, or $R^{73}$ and $R^{6'}$ taken together from a group —X— where X is $(CR^{81}R^{82})_{aa}$ or X is $(CR^{81}R^{82})_{ab}$—Y and Y is oxygen, sulfur or $CR^{81}$=$CR^{82}$;

$R^{74}$, $R^{75}$, $R^{76}$, $R^{79}$, $R^{80}$, $R^{81}$, and $R^{82}$ are independently hydrogen or $C_{1-6}$alkyl;

$R^{77}$ and $R^{78}$ are independently $C_{1-6}$alkyl;

y is 1 or 2;
z is 0, 1, or 2;
aa is 2, 3 or 4;
ab is 0, 1, 2 or 3;

alternatively, E represents group (h);

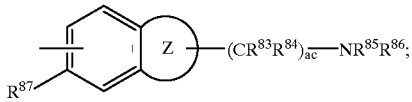

(h)

$R^{83}$ and $R^{84}$ are independently hydrogen or $C_{1-6}$alkyl;

$R^{85}$ and $R^{86}$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring which may contain an additional heteroatom selected from oxygen, nitrogen or sulfur, where optional substituents include $C_{1-6}$alkyl, aryl, $CONR^{88}R^{89}$, $NR^{90}R^{91}$, hydroxy, $OCOR^{92}$, $NHCOC_{0-6}$alkyl where alkyl is optionally substituted by OH, $NHCOCF_3$, $NHSO_2R^{93}$, and $NHCO_2R^{94}$;

$R^{87}$ is hydrogen or $C_{1-6}$alkyl, $C_{1-6}$alkoxy, or halogen, or $R^{87}$ together with $R^{6'}$ forms a group —AA— where AA is $(CR^{95}R^{96})_{ad}$ or AA is $(CR^{95}$=$CR^{96})_{ae}$—AB and AB is oxygen, sulfur, $CR^{95}$=$CR^{96}$, $CR^{95}$=N, $CR^{95}NR^{96}$ or N=N;

Z is an optionally substituted 5 to 7-membered heterocyclic ring containing 1 to 3 heteroatoms selected from oxygen, nitrogen or sulfur;

$R^{88}$, $R^{89}$, $R^{90}$, $R^{91}$, $R^{92}$, $R^{95}$, and $R^{96}$ are independently hydrogen or $C_{1-6}$alkyl;

$R^{93}$ and $R^{94}$ are independently $C_{1-6}$alkyl;

ac is 0 to 4;
ad is 1, 2 or 3;
ae is 0, 1, or 2;

alternatively, E represents group (i):

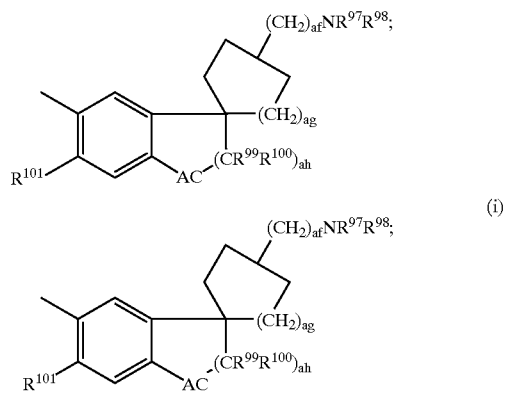

(i)

$R^{97}$ and $R^{98}$ are independently hydrogen, $C_{1-6}$alkyl, $C_{3-7}$cycloalkyl, aralkyl, or together with the nitrogen atom to which they are attached form an optionally substituted 5- to 7-membered heterocyclic ring which may contain an additional heteroatom selected from oxygen, nitrogen or sulfur, where optional substituents include $C_{1-6}$alkyl, aryl, $CONR^{102}R^{103}$, $NR^{104}R^{105}$, hydroxy, $OCOR^{106}$, $NHCOC_{0-6}$alkyl where alkyl is optionally substituted by OH, $NHCOCF_3$, $NHSO_2$ $R^{107}$, and $NHCO_2R^{108}$;

$R^{99}$ and $R^{100}$ are independently hydrogen or C1–6alkyl;

$R^{101}$ is hydrogen or $C_{1-6}$alkyl or $R^{101}$ and $R^{6'}$ together form a group —AD— where AD is $(CR^{109}R^{110})_{ai}$ or AD is $(CR^{109}R^{110})_{aj}$-AE and AE is oxygen, sulfur or $CR^{109}$=$CR^{110}$;

AC is oxygen, $CR^{111}R^{112}$ or $NR^{113}$ or AC is a group $S(O)_{ak}$;

$R^{102}$, $R^{103}$, $R^{104}$, $R^{105}$, $R^{106}$, $R^{109}$, $R^{110}$, $R^{111}$, $R^{112}$, and $R^{113}$ are independently hydrogen or $C_{1-6}$alkyl;

$R^{107}$ and $R^{108}$ are independently $C_{1-6}$alkyl:

af is 0, 1, 2, 3, or 4;
ag is 1, 2, or 3;
ah is 1, 2, 3 or 4;
ai is 2, 3 or 4;
aj is 0, 1, 2, or 3; and
ak is 0, 1 or 2.

DETAILED DESCRIPTION OF THE INVENTION

It has now been discovered that substituted anilides of formula (I) are CCR5 receptor modulators. It has also now been discovered that selective inhibition of CCR5 receptor mechanisms by treatment with the receptor modulators of formula (I), or a pharmaceutically acceptable salt thereof, represents a novel therapeutic and preventative approach to the treatment of a variety of disease states, including, but not limited to, COPD, asthma and atopic disorders (for example, atopic dermatitis and allergies), rheumatoid arthritis, atherosclerosis, sarcoidosis and other fibrotic disease, psoriasis, autoimmune diseases such as multiple sclerosis, and inflammatory bowel disease, all in mammals, preferably humans ("CCR5-mediated diseases"). Also, since CCR5 is a co-receptor for the entry of HIV into cells. selective receptor modulators may be useful in the treatment of HIV infection.

The term "alkyl" is used herein at all occurrences to mean a straight or branched chain radical of 1 to 6 carbon atoms, unless the chain length is limited thereto, including, but not limited to methyl, ethyl, n-propyl, isopropyl, n-butyl, sec-butyl, isobutyl, tert-butyl, and the like.

The terms "cycloalkyl" and "cyclic alkyl" are used herein at all occurrences to mean cyclic radicals, preferably comprising 3 to 7 carbon atoms which may be mono- or bicyclo-fused ring systems which may additionally include unsaturation, including, but not limited to, cyclopropyl, cyclopentyl, cyclohexyl, and the like.

The terms "halo" or "halogen" are used interchangeably herein at all occurrences to mean radicals derived from the elements chlorine, fluorine, iodine and bromine.

The term "heterocyclic ring" is used herein at all occurrences to mean a saturated or partially saturated 5-, 6-, or 7-membered ring system (unless the cyclic ring system is otherwise limited) in which the ring system contains one to 3 heteroatoms selected from oxygen, sulfur, or nitrogen, which ring system may be optionally substituted with $C_{1-6}$alkyl or $C_{3-7}$cycloalkyl. Examples of such rings include, but are not limited to, piperidine, tetrahydropyridine, and piperazine. When the heterocyclic ring is fused to a phenyl group, the term "heterocyclic ring", together with the phenyl ring to which it is fused, forms a ring which includes, but is not limited to, dihydro-1,4-benzoxazine and 1,2,3,4-tetrahydroquinoline, which may be optionally substituted by $C_{1-6}$alkyl or oxo.

The term "6,6 or 6,5 bicyclic ring" means a 6,6 or 6,5-bicyclic ring system containing a nitrogen atom and optionally a further heteroatom selected from nitrogen, oxygen, or sulfur, which ring system may be optionally substituted with $C_{1-6}$alkyl. Examples of such ring systems include, but are not limited to, tropane, isoquinuclidine and granatane rings.

The term "CCR5 mediated disease state" is used herein at all occurrences to mean any disease state which is mediated (or modulated) by CCR5.

The term "monocyclic heterocyclic ring" is used herein at all occurrences to mean a single aromatic ring of 5 to 7 members containing 1 to 3 heteroatoms selected from oxygen, nitrogen and sulfur represented by $P^1$ and/or $P^2$ include thienyl, furyl, pyrrolyl, and pyridyl.

The term "fused bicyclic heterocyclic ring" is used herein at all occurrences to mean a fused bicyclic aromatic ring system of 8 to 11-members containing 1 to 3 heteroatoms selected from oxygen, nitrogen and sulfur include indole, benzofuran, benzothiophene, quinoline, and isoquinoline rings.

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

The compounds of the invention can exist in unsolvated as well as solvated forms, including hydrated forms. In general, the solvated forms, with pharmaceutically acceptable solvents such as water, ethanol, and the like, are equivalent to the unsolvated forms for purposes of this invention.

The compounds of the present invention may contain one or more asymmetric carbon atoms and may exist in racemic and optically active forms. The stereocenters may be of any combination of R and S configuration, for example, (R,R), (R,S), (S,S) or (S,R). All of these compounds are within the scope of the present invention.

For the compounds of formula (I) various embodiments are as follows. It will be understood that the basic nitrogen in moiety E may be optionally quaternized with $C_{1-6}$alkyl or is optionally present as the N-oxide.

wherein:

$P^1$ and $P^2$ are suitably independently phenyl, fused bicyclic aryl, a monocyclic heterocyclic ring of 5- to 7-members containing 1 to 3 heteroatoms selected from oxygen, nitrogen and sulfur, or a fused bicyclic heterocyclic ring of 8 to 11-members containing 1 to 3 heteroatoms selected from oxygen, nitrogen or sulfur, providing that at least one of $P^1$ and $P^2$ is a heterocyclic group. Preferably, $P^1$ and $P^2$ are phenyl, pyrrolyl, thienyl, thiazolyl, 1,2,3-triazolyl, pyridyl, and benzodioxanyl, providing that at least one of $P^1$ or $P^2$ is a heterocyclic group. More preferably, $P^1$ and $P^2$ are phenyl, thienyl, and benzodioxanyl, providing that at least one of $P^1$ and $P^2$ is a heterocyclic group.

$P^3$ is suitably a monocyclic heterocyclic ring of 5- to 7-members containing 1 to 3 heteroatoms selected from oxygen, nitrogen and sulfur, or a fused bicyclic heterocyclic ring of 8 to 11-members containing 1 to 3 heteroatoms selected from oxygen, nitrogen or sulfur. $P^3$ is preferably thienyl, pyridyl, indolyl, benzofuranyl, benzothienyl, and benzopyranyl. More preferably, $P^3$ is indolyl, benzofuranyl, and benzopyranyl.

When $R^{1'}$ is a 5- to 7-membered heterocyclic ring containing 1 to 4 heteroatoms selected from oxygen, nitrogen, or sulfur, suitable heterocyclic rings include aromatic groups such as thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl, pyrazinyl, and dioxanyl. Saturated and partially saturated rings are also within the scope of the invention, in particular rings including an oxo or thioxo moiety such as lactams and thiolactams. Suitably, the heterocyclic ring can be linked to the remainder of the molecule via a carbon atom, or, when present, a nitrogen atom. Suitable substituents for these rings include one to two of $R^{3'}$.

L is a suitably group of formula —C(=V)—DR$^{6'}$—, —DR$^{7'}$—C(=V)—, —CH$_2$NH—, or —NHCH$_2$—. L is preferably —C(=V)—DR$^{6'}$—.

V is suitably oxygen or sulfur. V is preferably oxygen.

D is suitably nitrogen, carbon, or a CH group. D is preferably nitrogen.

$R^{1'}$, $R^{2'}$, and $R^{4'}$ are suitably independently hydrogen, $C_{1-6}$alkyl, $C_{2-6}$alkenyl, $C_{2-6}$alkynyl, $C_{3-7}$cycloalkyl, $C_{3-7}$cycloalkenyl, aryl, $(CH_2)_n$·NR$^{8'}$R$^{9'}$, $(CH_2)_d$·NR$^{8'}$COR$^{10'}$, $(CH_2)_n$·NR$^{8'}$CO$_2$R$^{11'}$, $(CH_2)_d$·NR$^{8'}$SO$_2$R$_{12'}$, $(CH_2)_d$·CONR$^{13'}$R$^{14'}$, hydroxy $C_{1-6}$alkyl, $C_{1-4}$alkoxyalkyl (optionally substituted by a $C_{1-4}$alkoxy or hydroxy group), $(CH_2)_d$·CO$_2$C$_{1-6}$alkyl, $(CH_2)_e$·OC(O)R$^{15'}$, CR$^{16'}$=NOR$^{17'}$, CNR$^{18'}$=NOR$^{17'}$, COR$^{19'}$, CONR$^{13'}$R$^{14'}$, CONR$^{13'}$(CH$_2$)$_f$OC$_{1-4}$alkyl, CONR$^{13'}$(CH$_2$)$_d$·CO$_2$R$^{20'}$, CONHNR$^{21'}$R$^{22'}$, CONR$^{13'}$SO$_2$R$^{23'}$, CO$_2$R$^{24'}$, cyano, trifluoromethyl, NR$^{8'}$R$^{9'}$, NR$^{8'}$COR$^{10'}$, NR$^{25'}$CO(CH$_2$)$_d$·NR$^{25'}$R$^{26'}$, NR$^{25'}$CONR$^{25'}$R$^{26'}$, NR$^{8'}$CO$_2$R$^{11'}$, NR$^{8'}$SO$_2$R$^{12'}$, N=CNR$^{25'}$NR$^{25'}$R$^{26'}$, nitro, hydroxy, $C_{1-6}$alkoxy, hydroxyC$_{1-6}$alkoxy, $C_{1-6}$alkoxyC$_{1-6}$alkoxy, OC(O) NR$^{27'}$R$^{28'}$, SR$^{29'}$, SOR$^{30'}$, SO$_2$R$^{30'}$, SO$_2$NR$^{31'}$R$^{32'}$, halogen, $C_{1-6}$alkanoyl, CO$_2$(CH$_2$)$_d$·OR$^{33'}$, or $R^{1'}$ is an optionally substituted 5 to 7-membered heterocyclic ring containing 1 to 4 heteroatoms selected from oxygen, nitrogen or sulfur. Preferably, $R^{1'}$, $R^{2'}$, and $R^{4'}$ are hydrogen, $C_{1-6}$alkyl, trifluoromethyl, or halogen.

$R^{3'}$ and $R^{5'}$ are suitably independently hydrogen, $C_{1-6}$alkyl, $C_{3-6}$cycloalkyl, $C_{3-6}$cycloalkenyl, hydroxyC$_{1-6}$alkyl, C$_{1-6}$alkylOC$_{1-6}$akyl, CONR$^{34'}$R$^{35'}$, CO$_2$R$^{36'}$, cyano, aryl, trifluoromethyl, NR$^{37'}$R$^{38'}$, nitro, hydroxy, C$_{1-6}$alkoxy, C$_{1-6}$alkanoyl, acyloxy, or halogen. Preferably, R$^{3'}$ and R$^{5'}$ are hydrogen, C$_{1-6}$alkyl, C$_{1-6}$alkoxy, or halogen.

R$^{16'}$, R$^{17'}$, R$^{18'}$, R$^{19'}$, R$^{20'}$, R$^{21'}$, R$^{22'}$, R$^{25'}$, R$^{26'}$, R$^{29'}$, R$^{33'}$, R$^{34'}$, R$^{35'}$, R$^{36'}$, R$^{37'}$, and R$^{38'}$ are suitably independently hydrogen or C$_{1-6}$alkyl.

R$^{6'}$ is suitably hydrogen or C$_{1-6}$alkyl, providing that D is nitrogen or a CH group. Preferably, R$^{6'}$ is hydrogen.

R$^{7'}$ is suitably hydrogen or C$_{1-6}$alkyl, providing that D is nitrogen or a CH group.

R$^{8'}$ and R$^{9'}$ are suitably independently hydrogen or C$_{1-6}$alkyl, or R$^{8'}$ and R$^{9'}$ together with the nitrogen to which they are attached, forms a 5- to 6-membered heterocyclic ring, which may optionally be substituted by an oxo group, and, when there are six members, may optionally contain in the ring one oxygen or one sulfur atom.

R$^{10'}$ is hydrogen, C$_{1-6}$alkyl, or C$_{1-4}$alkoxyalkyl.

R$^{11'}$, R$^{23'}$, and R$^{30'}$ are independently C$_{1-6}$alkyl.

R$^{12'}$ is C$_{1-6}$alkyl or phenyl.

R$^{13'}$ and R$^{14'}$ are independently hydrogen or C$_{1-6}$alkyl, or R$^{13'}$ and R$^{14'}$ together with the nitrogen to which they are attached form a 5- to 6-membered saturated heterocyclic ring which, when there are 6 ring members, may optionally contain in the ring one oxygen or one sulfur atom.

R$^{15'}$ is C$^{1-4}$alkyl, optionally substituted by C$_{1-6}$alkoxy.

R$^{24'}$ is hydrogen or C$_{1-6}$alkyl optionally substituted with one or two substituents selected from C$_{1-6}$alkyl, C$_{1-6}$alkoxy, hydroxy, or NR$^{8'}$R$^{9'}$.

R$^{27'}$ and R$^{28'}$ are independently hydrogen or C$_{1-6}$alkyl, or R$^{27'}$ and R$^{28'}$ together with the nitrogen to which they are attached form a 5- to 6-membered heterocyclic ring which, when there are six ring members, may optionally contain in the ring one oxygen or sulfur atom.

R$^{31'}$ and R$^{32'}$ are independently hydrogen or C$_{1-6}$alkyl, or R$^{31'}$ and R$^{33'}$ together with the nitrogen to which they are attached form 5- to 6-membered heterocyclic ring which, when there are six ring members, may optionally contain in the ring one oxygen or sulfur atom.

a' and b' are independently 1, 2, or 3.

c' is 0, 1, or 2.

d' is 1, 2, 3, or 4.

e' is 0, 1, 2, or 3.

f is 1, 2, or 3.

E suitably represents (a):

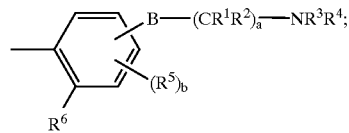

(a)

in which

B is suitably oxygen, S(O)$_c$, CR$^7$=CR$^8$, or CR$^7$R$^8$, or B is NR$^9$, B is preferably CR$^7$R$^8$, or oxygen. More preferably, B is CH$_2$ or oxygen.

R$^1$ and R$^2$ are suitably independently hydrogen or C$_{1-6}$alkyl; alternatively B(CR$^1$R$^2$)$_a$ is OCR$^1$R$^2$CR$^1$(OH)CR$^1$R$^2$ or OCR$^1$R$^2$CR$^1$(OCOCH$_3$)CR$^1$R$^2$. Preferably, R$^1$ and R$^2$ are hydrogen.

R$^3$ and R$^4$ are suitably independently hydrogen, C$_{1-6}$alkyl, C$_{3-7}$cycloalkyl, aralkyl, or together with the nitrogen atom to which they are attached form an optionally substituted 5- to 7-membered heterocyclic ring which may contain an additional heteroatom selected from oxygen, nitrogen or sulfur, where optional substituents include C$_{1-6}$alkyl, aryl, CONR$^{10}$R$^{11}$, NR$^{10}$R$^{11}$, hydroxy, OCOR$^{12}$, NHCOC$_{0-6}$alkyl where alkyl is optionally substituted by OH, NHCOCF$_3$, NHSO$_2$ R$^{13}$, and NHCO$_2$R$^{14}$. Preferably R$^3$ and R$^4$ are both C$_{1-6}$alkyl, or together with the nitrogen atom to which they are attached form an optionally substituted 5- to 7-membered heterocyclic ring which may contain an additional heteroatom selected from oxygen, nitrogen or sulfur. More preferably, R$^3$ and R$^4$ are C$_{3-6}$alkyl, or together with the nitrogen to which they are attached form a 6-membered ring, optionally substituted with one or more of C$_{1-6}$alkyl, N-acetamido, or hydroxy. Most preferably, R$^3$ and R$^4$ are isopropyl or R$^3$ is isopropyl and R$^4$ is tert-butyl, or together with the nitrogen to which they are attached are 1-(2,2,6,6-tetramethylpiperidinyl), 1-(4-acetamido-2,2,6,6-tetramethylpiperidinyl), 1-(4-hydroxy-2,2,6,6-tetramethylpiperidinyl), or 1-(4-hydroxy-2,2,4,6,6-pentamethylpiperidinyl).

Preferably, B-(CR$^1$R$^2$)$_a$-NR$^3$R$^4$ is ortho to R$^5$, meta to L, and para to R$^6$, and R$^5$ is para to L.

R$^5$ is suitably hydrogen, C$_{1-6}$alkyl, aryl, CN, CONR$^{15}$R$^{16}$, CO$_2$R$^{17}$, trifluoromethyl, NHCO$_2$R$^{18}$, hydroxy, C$_{1-6}$alkoxy, benzyloxy, OCH$_2$CO$_2$C$_{1-6}$alkyl, OCF$_3$, S(O)$_d$R$^{19}$, SO$_2$NR$^{20}$R$^{21}$, or halogen. R$^5$ is preferably C$_{1-6}$alkoxy, SC$_{1-6}$alkyl or halogen; more preferably methoxy, methylthio or iodo, most preferably methoxy. When R$^5$ is methoxy, it is preferably para to L.

R$^6$ is suitably hydrogen, C$_{1-6}$alkyl, aryl, trifluoromethyl, hydroxy, C$_{1-6}$alkoxy, or halogen, or R$^6$ taken together with R$^{6'}$ forms a group D where D is (CR$^{22}$R$^{23}$)$_e$ or D is (CR$^{22}$R$^{23}$)$_f$-G where G is oxygen, sulfur, or CR$^{22}$=CR$^{23}$, CR$^{22}$=N, =CR$^{22}$O, =CR$^{22}$S, or =CR$^{22}$—NR$^{23}$. Preferably, R$^6$ is hydrogen.

R$^7$, R$^8$, R$^{10}$, R$^{11}$, R$^{15}$, R$^{16}$, R$^{17}$, R$^{20}$, R$^{21}$, R$^{22}$, and R$^{23}$ independently hydrogen or C$_{1-6}$alkyl.

R$^9$ is hydrogen, C$_{1-6}$alkyl, or phenylC$_{1-6}$alkyl.

R$^{12}$, R$^{13}$, R$^{14}$, R$^{18}$, and R$^{19}$ are independently C$_{1-6}$alkyl.

a is suitably 1, 2, 3, or 4. Preferably, a is 2 or 3, more preferably, a is 2 or 3 when B is oxygen and a is 2 when B is CH$_2$, most preferably, a is 2 when B is oxygen.

b is suitably 1 or 2. Preferably, b is 1.

c and d are suitably independently 0, 1, or 2.

e is suitably 2, 3, or 4.

f is suitably 0, 1, 2, or 3.

alternatively, E suitably represents (b):

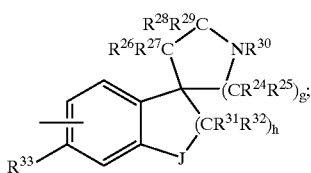

$R^{24}$, $R^{25}$, $R^{26}$, $R^{27}$, $R^{28}$, $R^{29}$, $R^{31}$, and $R^{32}$ are suitably independently hydrogen or $C_{1-6}$alkyl. $R^{24}$, $R^{25}$, $R^{26}$, $R^{27}$, $R^{28}$, $R^{29}$, $R^{31}$, and $R^{32}$ are preferably hydrogen.

$R^{30}$ is suitably hydrogen, $C_{1-6}$alkyl, or $C_{3-7}$cycloalkyl. Preferably, $R^{30}$ is $C_{1-6}$alkyl, more preferably, $R^{30}$ is $C_{3-6}$alkyl, most preferably, $R^{30}$ is isopropyl.

$R^{33}$ is suitably hydrogen, $C_{1-6}$alkyl, trifluoromethyl, hydroxy or halogen, or $R^{33}$ and $R^{6'}$ together form a group —K— where K is $(CR^{34}R^{35})_i$ or K is $(CR^{34}R^{35})_j$ —M and M is oxygen, sulfur, $CR^{34}$=$CR^{35}$, $CR^{34}$=N, or N=N. Preferably, $R^{33}$ is hydrogen.

J is suitably oxygen, $CR^{36}R^{37}$, or $NR^{38}$, or J is a group $S(O)_k$. Preferably, J is oxygen. Preferably, J is para to L.

$R^{34}$, $R^{35}$, $R^{36}$, $R^{37}$, $R^{38}$ are suitably independently hydrogen or $C_{1-6}$alkyl.

g is suitably 1, 2, or 3. Preferably, g is 2 or 3, more preferably 2.

h is suitably 1, 2, or 3. Preferably, h is 1.

i is suitably 2, 3, or 4.

j is suitably 0, 1, 2, or 3.

k is suitably 0, 1 or 2.

A preferred subgenus of the compounds of formula (I) are compounds of formula (Ia) and formula (Ib) in which $R^{1'}$, $R^{2'}$, $R^{3'}$, $R^{4'}$, $R^{5'}$, $p^1$, $p^2$, $p^3$, a', b', c', L, $R^{24}$, $R^{25}$, $R^{26}$, $R^{27}$, $R^{28}$, $R^{29}$, $R^{30}$, $R^{31}$, $R^{32}$, $R^{33}$, J, g, and h are define above:

Formula (Ia)

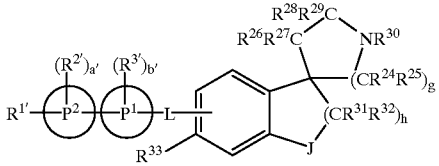

Formula (Ib)

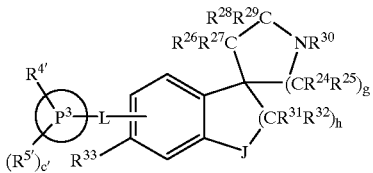

Among the preferred compounds of the invention are the following compounds:

N-[4-Methoxy-3-(4-methyl-1-piperazinyl)phenyl]-5-(4-pyridinyl)-2-furancarboxamide;
N-[4-Methoxy-3-(4-methyl-1-piperazinyl)phenyl]-5-(4-pyridyl)-thiophene-2-carboxamide;
N-[4-Methoxy-3-(4-methyl-1-piperazinyl)phenyl]-5-(4-pyridinyl)-3-furancarboxamide;
N-[4-Methoxy-3-(4-methyl-1-piperazinyl)phenyl]-3-methyl-4-(3-thienyl)-benzamide dioxalate;
4-Methoxy-N-[4-methoxy-3-(4-methyl-1-piperazinyl)phenyl]-5-(4-pyridinyl)-3-thiophenecarboxamide;
N-[4-Methoxy-3-(4-methyl-1-piperazinyl)phenyl]-4-(2-thienyl)-3-methylbenzamide oxalate;
N-[4-Methoxy-3-(4-methyl-1-piperazinyl)phenyl]-4-(4-phenyl-2-thiazolyl)benzamide;
N-[3-[2-[Bis(1-methylethyl)amino]ethoxy]-4-methoxyphenyl]-5-(1-pyrrolyl)pyridin-3-carboxamide;
N-[3-[2-[Bis(1-methylethyl)amino]ethoxy]-4-methoxyphenyl]-2-thiophenecarboxamide;
N-[3-[2-[Bis(1-methylethyl)amino]ethoxy]-4-methoxyphenyl]-3-pyridinecarboxamide;
6-Chloro-N-[3-[2-[bis(1-methylethyl)amino]ethoxy]-4-methoxyphenyl]-3-pyridinecarboxamide;
5-Bromo-N-[3-[2-[bis(1-methylethyl)amino]ethoxy]-4-methoxyphenyl]-3-pyridinecarboxamide;
N-[3-[2-(Diethylamino)ethoxy]-4-methoxyphenyl]-2-thiophenecarboxamide;
N-[3-[2-[Bis(1-methylethyl)amino]ethoxy]-4-methoxyphenyl]-4-(3-pyridinyl)benzamide;
N-[3-[2-[Bis(1-methylethyl)amino]ethoxy]-4-methoxyphenyl]-4-(2-pyridinyl)benzamide;
N-[3-[2-[Bis(1-methylethyl)amino]ethoxy]-4-methoxyphenyl]-4-(2-thiazolyl)-benzamide;
N-[3-[2-[Bis(1-methylethyl)amino]ethoxy]-4-methoxyphenyl]-6-phenyl-3-pyridinecarboxamide:
N-[3-[2-[Bis(1-methylethyl)amino]ethoxy]-4-methoxyphenyl]-4-(4-pyridinyl)benzamide;
N-[3-[2-[Bis(1-methylethyl)amino]ethoxy]-4-methoxyphenyl]-5-phenyl-2-pyridinecarboxamide;
N-[3-[2-[Bis(1-methylethyl)amino]ethoxy]-4-methoxyphenyl]-3-(2-thienyl)benzamide:
N-[3-[2-[Bis(1-methylethyl)amino]ethoxy]-4-methoxyphenyl]-4-(2-thienyl)benzamide;
N-[3-[2-[Bis(1-methylethyl)amino]ethoxy]-4-methoxyphenyl]-5-phenyl-2-thiophenecarboxamide:
N-[1'-Isopropyl-spiro[benzofuran-3(2H),4'-piperidin]-5-yl)-2-(2,3-dihydro-1,4-benzodioxan-2-yl)-4-thiazolecarboxamide;
N-[3-[2-[Bis(1-methylethyl)amino]ethoxy]-4-methoxyphenyl]-5-methyl-2-phenyl-2H-1,2,3-triazole-4-carboxamide;
N-[3-[2-[Bis(1-methylethyl)amino]ethoxy]-4-methoxyphenyl]-2-(2,3-dihydro-1,4-benzodioxin-2-yl)-4-thiazolecarboxamide;
N-[3-[2-(Diethylamino)ethoxy]-4-methoxyphenyl]-5-methyl-2-phenyl-2H-1,2,3-triazole-4-carboxamide;
N-[3-[2-(Diethylamino)ethoxy]-4-methoxyphenyl]-2-(2,3-dihydro-1,4-benzodioxin-2-yl)-4-thiazolecarboxamide;
N-[3-[2-(Dimethylamino)ethoxy]-4-methoxyphenyl]-2-(2,3-dihydro-1,4-benzodioxin-2-yl)-4-thiazolecarboxamide;
(+)-N-[3-[2-[Bis(1-methylethyl)amino]ethoxy]-4-methoxyphenyl]-2-(2,3-dihydro-1,4-benzodioxin-2-yl)-4-thiazolecarboxamide;
(−)-N-[3-[2-[Bis(1-methylethyl)amino]ethoxy]-4-methoxyphenyl]-2-(2,3-dihydro-1,4-benzodioxin-2-yl)-4-thiazolecarboxamide;
N-[3-[2-[Bis(1-methylethyl)amino]ethoxy]-4-methoxyphenyl]-4-methyl-2-[4-(trifluoromethyl)phenyl]-5-thiazolecarboxamide;
N-[3-[2-[Bis(1-methylethyl)amino]ethoxy]-4-methoxyphenyl]-2-(3-bromo-2-thienyl)-4-thiazolecarboxamide;
N-[3-[2-(Diethylamino)ethoxy]-4-methoxyphenyl]-2-(3-bromo-2-thienyl)-4-thiazolecarboxamide;
N-[3-[2-[Bis(1-methylethyl)amino]ethoxy]phenyl]-2-(3-bromo-2-thienyl)-4-thiazolecarboxamide;
N-[3-[2-[Bis(1-methylethyl)amino]ethoxy]-4-methoxyphenyl]-2-(2,3-dihydro-1,4-benzodioxin-2-yl)-4-methyl-5-thiazolecarboxamide;

N-[3-[2-(Diethylamino)ethoxy)-4-methoxyphenyl]-2-(2,3-dihydro-1,4-benzodioxin-2-yl)-4-methyl-5-thiazolecarboxamide;

N-[3-[2-[Bis(1-methylethyl)amino]ethoxy]phenyl]-2-(2,3-dihydro-1,4-benzodioxin-2-yl)-4-methyl-5-thiazolecarboxamide;

N-[3-[2-[Bis(1-methylethyl)amino]ethoxy]-4-methoxyphenyl]-2-phenyl-4-thiazolecarboxamide;

N-[3-[2-(Diethylamino)ethoxy]-4-methoxyphenyl]-2-phenyl-4-thiazolecarboxamide;

N-[3-[2-[Bis(1-methylethyl)amino]ethoxy]phenyl]-2-phenyl-4-thiazolecarboxamide;

N-[3-[2-[Bis(1-methylethyl)amino]ethoxy]-4-methoxyphenyl]-4-methyl-2-phenyl-5-thiazolecarboxamide;

N-[3-[2-(Diethylamino)ethoxy]-4-methoxyphenyl]-4-methyl-2-phenyl-5-thiazolecarboxamide;

N-[3-[2-[Bis(1-methylethyl)amino]ethoxy]phenyl]-4-methyl-2-(4-chlorophenyl)-5-thiazolecarboxamide;

N-[3-[2-[Bis(1-methylethyl)amino]ethoxy]-4-methoxyphenyl]-2-(4-chlorophenyl)-5-thiazolecarboxamide;

N-[3-[2-(Diethylamino)ethoxy]-4-methoxyphenyl]-2-(4-chlorophenyl)-5-thiazolecarboxamide;

N-[3-[2-[Bis(1-methylethyl)amino]ethoxy]-4-methoxyphenyl]-4-methyl-2-[3-(trifluoromethyl)phenyl]-5-thiazolecarboxamide;

N-[3-[2-(Diethylamino)ethoxy]-4-methoxyphenyl]-4-methyl-2-[3-(trifluoromethyl)phenyl]-5-thiazolecarboxamide;

N-[3-[2-[Bis(1-methylethyl)amino]ethoxy]phenyl]-4-methyl-2-[3-(trifluoromethyl)phenyl]-5-thiazolecarboxamide;

N-[3-[2-[Bis(1-methylethyl)amino]ethoxy]-4-methoxyphenyl]-2-[2-chloro-4-(trifluoromethyl)phenyl]-4-thiazolecarboxamide;

N-[3-[2-(Diethylamino)ethoxy]-4-methoxyphenyl]-2-[2-chloro-4-(trifluoromethyl)phenyl]-4-thiazolecarboxamide;

N-[3-[2-[Bis(1-methylethyl)amino]ethoxy]phenyl]-2-[2-chloro-4-(trifluoromethyl)phenyl]-4-thiazolecarboxamide;

N-[3-[2-[Bis(1-methylethyl)amino]ethoxy]-4-methoxyphenyl]-2-(2,3-dichlorophenyl)4-thiazolecarboxamide;

N-[3-[2-(Diethylamino)ethoxy]-4-methoxyphenyl]-2-(2,3-dichlorophenyl)-4-thiazolecarboxamide;

N-[3-[2-[Bis(1-methylethyl)amino]ethoxy]phenyl]-2-2,3-dichlorophenyl)-4-thiazolecarboxamide;

N-[3-[2-[Bis(1-methylethyl)amino]ethoxy]-4-methoxyphenyl]-2-[3-(trifluoromethyl)phenyl]-4-thiazolecarboxamide;

N-[3-[2-(Diethylamino)ethoxy]-4-methoxyphenyl]-2-[3-(trifluoromethyl)phenyl]-4-thiazolecarboxamide;

N-[3-[2-[Bis(1-methylethyl)amino]ethoxy]phenyl]-2-[3-(trifluoromethyl)phenyl]-4-thiazolecarboxamide;

N-[3-[2-[Bis(1-methylethyl)amino]ethoxy]-4-methoxyphenyl]-4-methyl-2-pyrazinyl-5-thiazolecarboxamide;

N-[3-[2-(Diethylamino)ethoxy]-4-methoxyphenyl]-4-methyl-2-[4-(trifluoromethyl)phenyl]-5-thiazolecarboxamide;

N-[3-[2-[Bis(1-methylethyl)amino]ethoxy]-4-methoxyphenyl]-4-methyl-2-(4-chlorophenyl)-5-thiazolecarboxamide;

N-[3-[2-[Bis(1-methylethyl)amino]ethoxy]-4-methoxyphenyl]-3-chloro-benzo[b]thiophene-2-carboxamide;

N-[3-[3-[Bis(1-methylethyl)amino]propyl]-4-methoxyphenyl]-3-chloro-benzo[b]thiophene-2-carboxamide;

N-[3-[3-[Bis(1-methylethyl)amino]propoxy]-4-methoxyphenyl]-3-chloro-benzo[b]thiophene-2-carboxamide;

N-[3-[2-[Bis(1-methylethyl)amino]ethoxy]-4-methoxyphenyl]-6-chloro-2H-1-benzopyran-3-carboxamide;

N-[3-[3-[Bis(1-methylethyl)amino]propyl]-4-methoxyphenyl]-6-chloro-2H-1-benzopyran-3-carboxamide;

N-[3-[3-[Bis(1-methylethyl)amino]propoxy]-4-methoxyphenyl]-6-chloro-2H-1-benzopyran-3-carboxamide;

N-[3-[2-[Bis(1-methylethyl)amino]ethoxy]-4-methoxyphenyl]-5-chloro-1H-indole-2-carboxamide; and N-[3-[2-[Bis(1-methylethyl)amino]ethoxy]-4-methoxyphenyl]-5-chloro-2-benzofurancarboxamide.

Among the more preferred compounds of the invention are the following compounds:

N-[3-[2-[Bis(1-methylethyl)amino]ethoxy]-4-methoxyphenyl]-4-(2-thienyl)benzamide;

N-[3-[2-(Diisopropylamino)ethoxy]-4-methoxyphenyl]-5-phenyl-2-thiophenecarboxamide;

N-[1'-Isopropyl-spiro[benzofuran-3(2H),4'-piperidin-5-yl)-2-(2,3-dihydro-1,4-benzodioxan-2-y])-4-thiazolecarboxamide;

N-[3-[2-[Bis(1-methylethyl)amino]ethoxy]-4-methoxyphenyl]-2-(2,3-dihydro-1,4-benzodioxin-2-yl)-4-thiazolecarboxamide;

(+)-N-[3-[2-[Bis(1-methylethyl)amino]ethoxy]-4-methoxyphenyl]-2-(2,3-dihydro-1,4-benzodioxin-2-yl)-4-thiazolecarboxamide;

(−)-N-[3-[2-[Bis(1-methylethyl)amino]ethoxy]-4-methoxyphenyl]-2-(2,3-dihydro-1,4-benzodioxin-2-yl)-4-thiazolecarboxamide;

N-[3-[2-[Bis(1-methylethyl)amino]ethoxy]-4-methoxyphenyl]-6-chloro-2H-1-benzopyran-3-carboxamide;

N-[3-[3-[Bis(1-methylethyl)amino]propoxy]-4-methoxyphenyl]-6-chloro-2H-1-benzopyran-3-carboxamide;

N-[3-[2-[Bis(1-methylethyl)amino]ethoxy]-4-methoxyphenyl]-5-chloro-1H-indole-2-carboxamide; and N-[3-[2-[Bis(1-methylethyl)amino]ethoxy]-4-methoxyphenyl]-5-chloro-2-benzofurancarboxamide.

Among the compounds specifically excluded from the scope of this invention are the following compounds:

N-[4-Methoxy-3-(4-methyl-1-piperazinyl)phenyl]-3-methyl4-(4-pyridinyl)benzamide;

N-[4-Methoxy-3-(4-methyl-1-piperazinyl)phenyl]-4-(4-pyridinyl)benzamide dioxalate;

N-[4-Methoxy-3-(1-piperazinyl)phenyl]-3-methyl-4-(4-pyridinyl)benzamide;

N-[4-Methoxy-3-(4-ethyl-1-piperazinyl)phenyl]-3-methyl-4-(4-pyridinyl)benzamide oxalate;

N-[4-Methoxy-3-(4-benzyl 1-piperazinyl)phenyl]-3-methyl4-(4-pyridinyl)benzamide oxalate;

N-[4-(1-Methyl-3-piperidinyl)methoxyphenyl]-3-methyl-4-(4-pyridinyl)benzamide;

N-[4-Methoxy-3-(4-methyl-1-piperazinyl)phenyl]-5-(2-pyridinyl)-2-thiophenecarboxamide oxalate;

N-[4-Methoxy-3-(4-methyl-1-piperazinyl)phenyl]-4-(4-methoxyphenyl-2-thiazolyl)benzamide;

N-[3-[2-(Dimethylamino)ethoxy]-4-methoxyphenyl]-3-methyl-4-(4-pyridinyl)benzamide;

N-[4-Methoxy-3-(4-methyl-1-piperazinyl)phenyl]-5-(3-pyridinyl)-3-thiazolecarboxamide;

1'-Methyl-5- {4-[2-methyl-6-(2-oxopyrrollidin-1-yl)pyrid-3-yl]benzoyl}-2,3,6,7-tetrahydrospiro[furo[2,3-f]indole-3,4'-piperidine]hydrochloride;

N-[3-[2-[Bis(1-methylethyl)amino]ethoxy]-4-methoxyphenyl]-5-nitro-2-furancarboxamide;

N-[3-[2-[Bis(1-methylethyl)amino]ethoxy]-4-methoxyphenyl]-2-furancarboxamide;

N-[3-[2-(Diethylamino)ethoxy]-4-methoxyphenyl]-5-nitro-2-furancarboxamide;

N-[3-[2-(Diethylamino)ethoxy]-4-methoxyphenyl]-2-furancarboxamide;

N-[3-[2-(Diethylamino)ethoxy]-4-methoxyphenyl]-3-pyridinecarboxamide;

6-Chloro-N-[3-[2-(diethylamino)ethoxy]-4-methoxyphenyl]-3-pyridinecarboxamide;

5-Bromo-N-[3-[2-(diethylamino)ethoxy]-4-methoxyphenyl]-3-pyridinecarboxamide;

N-[3-[2-(Dimethylamino)ethoxy]-4-methoxyphenyl]-5-methyl-2-phenyl-2H-1,2,3-triazole4-carboxamide;

N-[3-[2-(Dimethylamino)ethoxy]-4-methoxyphenyl]-2-thiophenecarboxamide;

N-[3-[2-(Dimethylamino)ethoxy]-4-methoxyphenyl]-5-nitro-2-furancarboxamide;

N-[3-[2-(Dimethylamino)ethoxy]-4-methoxyphenyl]-2-furancarboxamide;

6-Chloro-N-[3-[2-(dimethylamino)ethoxy]-4-methoxyphenyl]-3-pyridinecarboxamide;

5-Bromo-N-[3-[2-(dimethylamino)ethoxy]-4-methoxyphenyl]-3-pyridinecarboxamide.

N-[3-[2-[Bis(1-methylethyl)amino]ethoxy]-phenyl]-4-methyl-2-[4-(trifluoromethyl)phenyl]-5-thiazolecarboxamide;

N-[3-[2-(Diethylamino)ethoxy]-4-methoxyphenyl]-2-(4-methyl-1,2,3-thiadiazol-5-yl)-4-thiazolecarboxamide;

N-[3-[2-[Bis(1-methylethyl)amino]ethoxy]phenyl]-4-methyl-2-phenyl-5-thiazolecarboxamide;

N-[3-[2-[Bis(1-methylethyl)amino]ethoxy]-4-methoxyphenyl]-4-methyl-2-(2-pyridinyl)-5-thiazolecarboxamide;

N-[3-[2-[Bis(1-methylethyl)amino]ethoxy]phenyl]-2-(2,3-dichlorophenyl)-4 -thiazolecarboxamide;

N-[3-[2-[Bis(1-methylethyl)amino]ethoxy]-4-methoxyphenyl]-4-methyl-2-(2-pyrazinyl)thiazole-5-carboxamide;

N-[3-[2-[Bis(1-methylethyl)amino]ethoxy]-4-methoxyphenyl]-4-methyl-2-(3-pyridinyl)4-thiazolecarboxamide;

N-[3-[2-(Diethylamino)ethoxy]-4-methoxyphenyl]-4-methyl-2-(3-pyridinyl)-4-thiazolecarboxamide:

N-[3-[2-[Bis(1-methylethyl)amino]ethoxy]phenyl]-4-methyl-2-(3-pyridinyl)-4-thiazolecarboxamide:

N-[3-[2-[Bis(1-methylethyl)amino]ethoxy]-4-methoxyphenyl]-2-(4-methyl-1,2,3-thiadiazol-5-yl)-4-thiazolecarboxamide;

N-[3-[2-[Bis(1-methylethyl)amino]ethoxy]phenyl]-2-(4-methyl-1,2,3-thiadiazol-5-yl)-4-thiazolecarboxamide;

N-[3-[2-[Bis(1-methylethyl)amino]ethoxy]-4-methoxyphenyl]-2-(4-chlorophenyl)-4-methyl-5-thiazolecarboxamide;

N-[3-[2-[Bis(1-methylethyl)amino]ethoxy]phenyl]-2-(4-chlorophenyl)-4-methyl-5-thiazolecarboxamide;

N- [3-[2-[Bis(1-methylethyl)amino]ethoxy]-4-methoxyphenyl]-2-(4-pyridinyl)-4-thiazolecarboxamide;

N-[3-[2-(Diethylamino)ethoxy]-4-methoxyphenyl]-2-(4-pyridinyl)-4-thiazolecarboxamide;

N-[3-[2-[Bis(1-methylethyl)amino]ethoxy]phenyl]-2-(4-pyridinyl)-4-thiazolecarboxamide;

N-[3-[2-(Diethylamino)ethoxy]-4-methoxyphenyl]-4-methyl -2-(3-pyridinyl)-5-thiazolecarboxamide;

N-[3-[2-[Bis(1-methylethyl)amino]ethoxy]-4-methoxyphenyl]-4-methyl-2-(4-pyridinyl)-5-thiazolecarboxamide;

N-[3-[2-(Diethylamino)ethoxy]-4-methoxyphenyl]-4-methyl-2-(4-pyridinyl)-5-thiazolecarboxamide; and N-[3-[2-[Bis(1-methylethyl)amino]ethoxy]phenyl]-4-methyl-2-(4-pyridinyl)-5-thiazolecarboxamide.

A subgenus of formula (I) wherein E is (a); B is meta to L: B—$(CR^1R^2)_a$—$NR^3R$ is —$(CH_2)_3N(CH_3)(C_{0-3}alkyl)$; $R^5$ is hydrogen, methyl, hydroxy, $C_{1-3}$alkoxy, halogen; $R^6$ is hydrogen, hydroxy, methoxy; L is CONH, NHCO or $NHCH_2$; Ar is (i); $R^{3'}$ is hydrogen; $P^1$ is phenyl and $P^2$ is attached in the 4-position; $P^2$ is 2-furyl, 2-thienyl, imidazol-4-yl, 1,2,4-triazol-3-yl, 2-, 3-, or 4-pyridinyl; $R^{1'}$ and $R^{2'}$ are independently hydrogen, methyl, hydroxymethyl, 1-(hydroxy)ethyl, formyl, acetyl, carboxamido, carboxy, carbomethoxy; $R^{3'}$ is hydrogen, has been described in GB 2276163, published Sep. 21, 1994, and GB 2276164, published Sep. 21, 1994; as 5-HT antagonists.

A compound of formula (I) wherein: E is (a); B is meta to L; B—$(CR^1R^2_a$—$NR^3R$ is —O—$(CH_2)_2N(CH_3)_2$; $R^5$ is iodo; $R^6$ is hydrogen; L is CONH; Ar is (ii); $R^{4'}$ and $R^{5'}$ are hydrogen; $P^3$ is 4-quinolinyl has been described in international patent application number WO 98/50343, published Nov. 12, 1998, as a 5-HT receptor antagonist.

A subgenus of formula (I) wherein: E is (b); $R^{24}$, $R^{25}$, $R^{26-29}$, $R^{31-32}$ are hydrogen; $R^{30}$ is hydrogen, methyl; J is para to L; J is oxygen; g is 2; h is 1, $R^{33}$ and $R^{6'}$ together are —$(CH_2)_2$—; Ar is (i); $P^2$ is phenyl and $P_1$ is attached at the 4-position; $P^1$ is 3-pyridinyl; $R^{1'}$ is 2-oxo-1-pyrrolidinyl, 1,3,4-oxadiazol-2-yl; $R^{2'}$ is methyl; $R^{3'}$ is hydrogen has been described in international patent application number WO 97/17351, published May 15, 1997 as 5-HT receptor antagonists.

A subgenus of formula (I) wherein: E is (c); Q is ortho to L; Q—$(CR^{39}R^{40})_1$—$R^{41}$ is $(CH_2)_2$-2-piperidinyl; $R^{47}$ is methyl; $R^{42}$, $R^{43}$, $R^{3'}$, and $R^{4'}$ are hydrogen; L is CONH; $P^3$ is 3-furyl, 2-thienyl, 2-, 3-, and 4-pyridinyl, have been described in U.S. Pat. No. 3,93 1195, published Jan. 6, 1976, and U.S. Pat. No. 4,000,143, published Dec. 28, 1976, and reported to have antiserotonin activity.

A subgenus of formula (I) wherein: E is (g); $R^{71}$ is meta to L; $R^{71}$ is ($C_{0-2}$alkyl-1-piperazine); $R^{72}$ is hydrogen, methyl, hydroxy, $C_{1-4}$alkoxy, halogen; $R^{73}$ is hydrogen, hydroxy, methoxy, or fluoro; $R^{1'}$, and $R^{2'}$ are hydrogen, methyl, acetyl; $R^{3'}$ is hydrogen, methyl, nitro, hydroxy, methoxy, or fluoro; $R^{4'}$ and $R^{5'}$ are independently hydrogen, methoxy, bromo; L is CONH or NHCO; Ar is (i) or (ii); $P^1$ is phenyl and $P^2$ is attached at the 4-position, or 2,5-furyl, 3,5-furyl, 2,5-thienyl, 3,5-thienyl, 3,6-pyridinyl, 1,4-naphthalenyl, 1,5-naphthalenyl; $P^2$ is 2-furyl, 3-thienyl, 2-, 3-, or 4-pyridinyl, 5-pyrimidinyl, 1,2,4-oxadiazol-3-yl, pyrazol-1-yl, 1,2,4-triazol-1-yl, imidazol-1-yl; $P^3$ is 2-, and 3-furyl, 2-thienyl, 3-thienyl, 2,5-thienyl, 3-pyridinyl, 4-quinolinyl; has been described in in EP 533267, published Mar. 24, 1993, GB 2273930, published Jul. 6, 1994; GB 2276164, published Sep. 21, 1994; international patent application number WO 95/04729, published Feb. 16, 1995: international patent application number WO 95/06644, published Mar. 9, 1995; international patent application number WO 98/47885, published Oct. 29, 1998, as 5-HT receptor antagonists.

A compound of formula (I) wherein: E is (g); $R^{71}$ is meta to L: $R^{71}$ is (methyl-1-piperazine); $R^{72}$ is 4-methoxy; $R^{73}$ is hydrogen: L is $CONR^{6'}$; $R^{73}$ and $R^{6'}$ are —$(CH_2)_2$—; Ar is (ii); $R^{4'}$ and $R^{5'}$ are independently methoxy or bromo; $P^3$ is 3-thienyl; has been described in international patent application number WO 95/06637, published Mar. 9, 1995 as a 5-HT receptor antagonist.

A subgenus of formula (I) wherein: the basic nitrogen in moiety E may be optionally quaternized with $C_{1-6}$alkyl or is optionally present as the N-oxide. E is (b). J is $CH_2$. g is 1, 2, or 3. h is 1, 2, or 3. $R^{24}$, $R^{25}$, $R^{26}$, $R^{27}$, $R^{28}$, $R^{29}$, $R^{31}$, and $R^{32}$ are hydrogen. $R^{30}$ is hydrogen or $C_{1-6}$alkyl. $R^{33}$ is hydrogen, $C_{1-6}$alkyl, trifluoromethyl, or halogen. L is $CONR^{8'}$, or $NR^9 CO$. $R^{8'}$ and $R^{9'}$ are independently hydrogen or $C_{1-6}$alkyl. $P^1$ is phenyl. $P^2$ is heteroaryl, wherein heteroaryl is selected from the group consisting of benzimidazolyl, benzofuranyl, benzooxazolyl, furanyl, imidazolyl, indolyl, isoxazolyl, isothiazolyl, oxadiazoyl, oxazolyl, pyrazinyl, pyrazolyl, pyridyl, pyrimidyl, pyrrolyl, quinolyl, thiadiazolyl, thiazolyl, thienyl or triazolyl. $R^{1*}$ is hydrogen, $R^{2*}$ is hydrogen or 1, 2, or 3 of hydroxy, cyano, halogen, trifluoromethyl, $NR^{8*}COR^{10*}$, $NR^{8*}CO_2R^{11*}$, $NR^{25*}CONHR^{25*}$, $NHS(O)_{0-2}R^{12*}$, $CONR^{13*}R^{14*}$, $COC_{1-5}$alkyl, $CO_2R^{24*}$, $C_{1-6}$alkoxy, $SR^{29*}$, $SOR^{30*}$, $SO_2R^{30*}$, or phenyl. $R^{3*}$ is hydrogen or 1 or 2 of hydroxy, cyano, halogen, trifluoromethyl, $CONR^{34*}R^{35*}$, $COC_{1-5}$alkyl, $CO_2R^{36*}$, $C_{1-6}$alkoxy, or phenyl $R^{8*}$, $R^{13*}$ $R^{14*}$, $R^{25*}$, $R^{29*}$, $R^{34*}$, $R^{35*}$, and $R^{36*}$ are independently hydrogen or $C_6$alkyl. $R^{10*}$ is hydrogen $C_{1-6}$alkyl, or $C_{1-4}$alkoxy$C_{1-6}$alkyl. $R^{11*}$ and $R^{30*}$ are independently $C_{1-6}$alkyl. $R^{12*}$ is $C_{1-6}$alkyl or phenyl. $R^{24*}$ is hydrogen or $C_{1-6}$alkyl optionally substituted with one or two of hydroxy or $C_{1-6}$alkoxy, has been described in WO 98/25604, published Jun. 18, 1998, as chemokine receptor modulators.

A subgenus of formula (I) wherein: the basic nitrogen in moiety E may be optionally quaternized with $C_{1-6}$alkyl or is optionally present as the N-oxide. E is (b). J is $CH_2$. g is 1, 2, or 3. h is 1, 2, or 3. $R^{24}$, $R^{25}$, $R^{26}$, $R^{27}$, $R^{28}$, $R^{29}$, $R^{31}$, and $R^{32}$ are hydrogen. $R^{30}$ is hydrogen or $C_{1-6}$alkyl. $R^{33}$ is hydrogen, $C_{1-6}$alkyl, trifluoromethyl, or halogen. L is $CH_2NH$. $P^1$ and $P^3$ are heteroaryl, wherein heteroaryl is selected from the group consisting of benzimidazolyl, benzofuranyl, benzooxazolyl, furanyl, imidazolyl, indolyl, isoxazolyl, isothiazolyl, oxadiazolyl, oxazolyl, pyrazinyl, pyrazolyl, pyridyl, pyrimidyl, pyrrolyl, quinolyl, thiadiazolyl, thiazolyl, thienyl or triazolyl. $P^2$ is phenyl. $R^{1*}$ and $R^{2*}$ are hydrogen. $R^{3*}$ and $R^{5*}$ are hydrogen or 1 or 2 of hydroxy, cyano, halogen, trifluoromethyl, $CONR^{34*}R^{35*}$, $COC_{1-5}$alkyl, $CO_2R^{36*}$, $C_{1-6}$alkoxy, or phenyl. $R^{4*}$ is hydrogen or 1 of hydroxy, cyano, halogen, trifluoromethyl, $NR^{8*}COR^{10*}$, $NR^{8*}CO_2R^{11*}$, $NR^{25*}CONHR^{25*}$, $NHS(O)_{0-2}R^{12*}$, $CONR^{13*}R^{14*}$, $COC_{1-5}$alkyl, $CO_2R^{24*}$, C1– 6alkoxy, $SR^{29*}$, $SOR^{30*}$, $SO_2R^{30*}$, or phenyl, $R^{8*}$, $R^{13*}R^{14*}$, $R^{25*}$, $R^{29*}$, $R^{34*}$, $R^{35*}$, and $R^{36*}$ are independently hydrogen or $C_{1-6}$alkyl. $R^{10*}$ is hydrogen $C_{1-6}$alkyl, or $C_{1-4}$alkoxy$C_{1-6}$alkyl. $R^{11*}$ and $R^{30*}$ are independently $C_{1-6}$alkyl. $R^{12*}$ is $C_{1-6}$alkyl or phenyl. $R^{24*}$ is hydrogen or $C_{1-6}$alkyl optionally substituted with one or two of hydroxy or $C_{1-6}$alkoxy, has been described in WO 98/25605, published Jun. 18, 1998, as chemokine receptor modulators.

Formulation of Pharmaceutical Compositions

The pharmaceutically effective compounds of this invention (and the pharmaceutically acceptable salts thereof) are administered in conventional dosage forms prepared by combining a compound of this invention ("active ingredient") in an amount sufficient to treat COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, ("CCR5-mediated disease states") with standard pharmaceutical carriers or diluents according to conventional procedures well known in the art. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment or prophylaxis of CCR5 mediated disease states. The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface active agent such as an anionic, cationic or non-ionic surfactant such as esters or polyoxyethylene derivatives thereof. Suspending agents such as natural gums, cellulose derivatives or inorganic materials such as silicaceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1 mg to about 10 mg per day.

In one aspect, this invention relates to a method of treating COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans, which comprises administering to such mammal an effective amount of a CCR5 receptor modulator, in particular, a compound of this invention.

By the term "treating" is meant either prophylactic or therapeutic therapy. Such compound can be administered to such mammal in a conventional dosage form prepared by combining the compound of this invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The compound is administered to a mammal in need of treatment for COPD, asthma and atopic disorders (for example, atopic dermatitis and allergies), rheumatoid arthritis, atherosclerosis, psoriasis, autoimmune diseases such as multiple sclerosis, inflammatory bowel disease, and HIV infection, in an amount sufficient to decrease symptoms associated with these disease states. The route of administration may be oral or parenteral.

The term parenteral as used herein includes intravenous, intramuscular, subcutaneous, intra-rectal, intravaginal or intraperitoneal administration, The subcutaneous and intramuscular forms of parenteral administration are generally preferred, The daily parenteral dosage regimen will preferably be from about 30 mg to about 300 mg per day of active ingredient, The daily oral dosage regimen will preferably be from about 100 mg to about 2000 mg per day of active ingredient, It will be recognized by one of skill in the art that the optimal quantity and spacing of individual dosages of a compound of this invention will be determined by the nature and extent of the condition being treated, the form, route and site of administration, and the particular mammal being treated, and that such optimums can be determined by conventional techniques, It will also be appreciated by one of skill in the art that the optimal course of treatment, i,e., the number of doses of the compound given per day for a defined number of days, can be ascertained by those skilled in the art using conventional course of treatment determination tests, Methods of Preparation Compounds of formula (I) are prepared by condensing suitably substituted heteroaryl carboxylic acids and suitably substituted anilines, which are commercially available or synthesized by methods known to the art from commercially available starting materials, using methods known to the art, For example, suitably substituted heteroaryl carboxylic acids, are treated with a suitable reagent, such as thionyl chloride, at a suitable temperature, such as at reflux, to afford heteroaryl carbonyl chlorides, and the acid chlorides are condensed with suitably substituted anilines in the presence of a suitable base, such as diisopropylethylamine, in a suitable solvent, such as dichloromethane, to give compounds of formula (I). Many additional methods for converting a carboxylic acid to an amide are known, and can be found in standard reference books, such as "Compendium of Organic Synthetic Methods", Vol. I–VI (published by Wiley-Interscience).

Specifically, compounds of this invention were prepared according to the methods described herein and by the methods of: U.S. Pat. No. 3,931,195, published Jan. 6, 1976, U.S. Pat. No. 4,000,143, published Dec. 28, 1976, EP 533267, published Mar. 24, 1993; GB 2273930, published Jul. 6, 1994; GB 2276163, published Sep. 21, 1994; GB 2276164, published Sep. 21, 1994; international patent application number WO 95/04729, published Feb. 16, 1995; international patent application number WO 95/06637, published Mar. 9, 1995; international patent application number WO 95/06644, published Mar. 9, 1995; international patent application number WO 97117351, published May 15, 1997; international patent application number WO 98/47885, published Oct. 29, 1998; and international patent application number WO 98/50343, published Nov. 12, 1998.

Compounds of this invention are also prepared using solid-phase chemistry as described herein and using the general method described in international patent application WO 99/01127, published Jan. 14, 1999. As describe in Scheme I, appropriately substituted (2-alkylamino)ethoxy-anilines I-2, such as 3-[2-(diisopropylamino)ethoxy]-4-methoxyaniline, synthesized from commercially available 2-methoxy-5-nitrophenol, I-1, according to the procedures described in WO 99/01127, are reacted with 4-formyl-3,5-dimethoxyphenol-Merrifield resin 1-3 (Boojamra, et al., *J. Org. Chem.* 1995, 60, 5742) and a suitable reducing agent, such as sodium triacetoxyborohydride, in a suitable solvent, such as dimethylformamide containing 1% acetic acid, to afford I-4. The resin-bound aniline I-4 is condensed with an appropriately substituted heteroaryl carboxylic acid I-5, which are commercially available or synthesized by methods known to the art, using a suitable activating agent, such as N-bromosuccinimide and triphenylphosphine, in a suitable solvent, such as dichloromethane, dimethylformamide and pyridine, to afford I-6. For example, 1-4 is treated with a ten-fold excess of an equimolar mixture of a 3-heteroaryl carboxylic acid, triphenylphosphine and N-bromosuccinimide, in a suitable solvent, such as dichloromethane, after which a ten-fold excess of a suitable base, such as pyridine, is added, and the mixture is gently agitated for a suitable time, for example forty-eight hours, to afford the resin-bound amide 1-6. Optionally, dimethylformamide may be added to the resulting mixture to increase the solubility of the heteroaryl carboxylic acid. Treatment of I-6 with a suitable acid and solvent, such as trifluoroacetic:dichloromethane:water (50:48:2) gives I-7 which are compounds of this invention.

Scheme I:

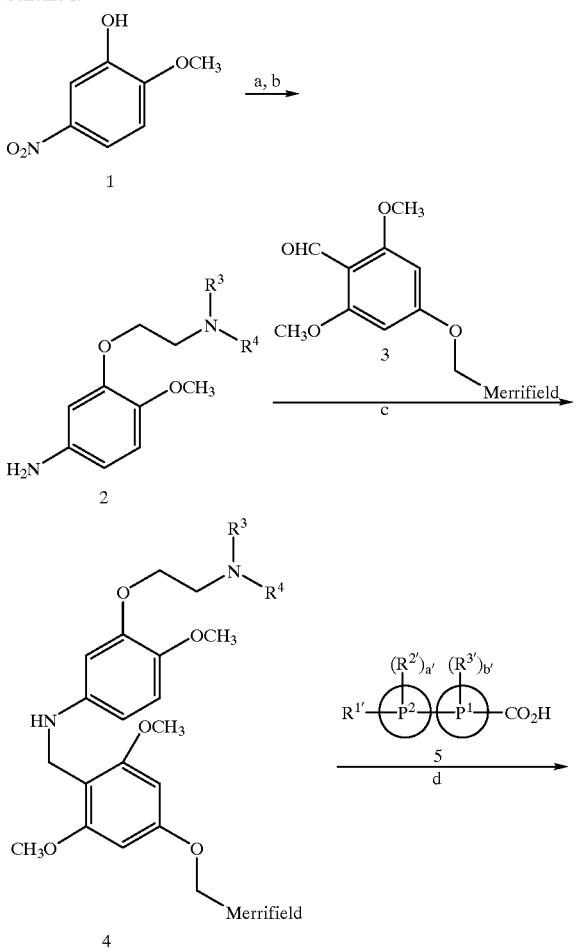

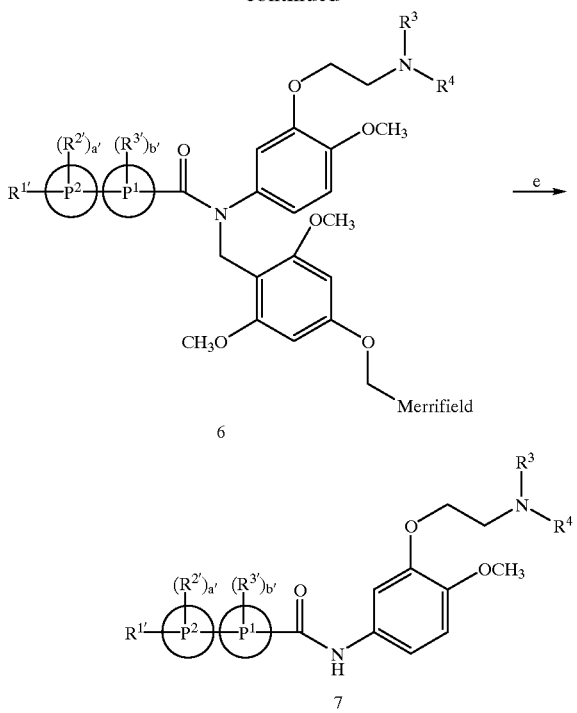

(a) $Cl(CH_2)_2NR^3R^4$, $K_2CO_3$, $CH_3COCH_3$; (b) $H_2$, 5% Pd/C, MeOH; (c) Merrifield resin bound aldehyde (3), $NaBH(OAc)_3$, 1% HOAc/DMF; (d) 3-aryl- or heteroarylcarboxylic acid, N-bromosuccinimide, $Ph_3P$, pyridine, $CH_2Cl_2$; (e) TFA, $CH_2Cl_2$, $H_2O$ The invention will now be described by reference to the following examples which are merely illustrative and are not to be construed as a limitation of the scope of the present invention. In the Examples, mass spectra were performed upon a VG Zab mass spectrometer using fast atom bombardment, unless otherwise indicated.

EXAMPLES

Preparation 1

Preparation of 4-(3-Pyridinyl)benzoyl Chloride a) 4-(3-pyridinyl)benzoic acid

A mixture of 4-carboxybenzeneboronic acid (0.5 g, 2.9 mmol), 3-bromopyridine (0.46 g, 2.9 mmol), sodium carbonate (1.37 g), and tetrakis(triphenylphosphine)palladium (0) (0.1 g) in 50% aqueous 1,2-dimethoxyethane (70 mL) was heated to reflux for 16 h, cooled, acidified, and extracted with dichloromethane. The organic phase was dried and concentrated in vacuo to yield the title compound, which was used without further purification.

b) 4-(3-pyridinyl)benzoyl chloride

The compound of Preparation 1(a) (0.2 g, 1 mmol) was refluxed in thionyl chloride (5 mL) for 30 min, the mixture was concentrated in vacuo, treated with dichloromethane, and concentrated in vacuo to afford the title compound.

Preparation 2

Preparation of 4-(2-Pyridinyl)benzoyl Chloride a) ethyl 4-(2-pyridinyl)benzoate 4-(Ethoxycarbonyl)phenylzinc iodide in tetrahydrofuran (0.5M, 2 mL, 1 mmol) was added to a solution of 2-bromopyridine (0.16 g, 1 mmol) and tetrakis(triphenylphosphine)palladium(0) (63 mg, 0.05 mmol) in tetrahydrofuran (5 mL) and stirred at RT for 3 h. The reaction was quenched with saturated ammonium chloride and extracted three times with ethyl acetate. The combined organic phase was dried (MgSO$_4$), concentrated in vacuo, and the residue chromatographed (silica gel, 10% ethyl acetate/hexane) to give the title compound as a yellow solid (0.15 g).

b) 4-(2-pyridinyl)benzoic acid

The compound of Preparation 2(a) (0.15 g. 0.66 mmol) was dissolved in ethanol (5 mL), treated with concentrated hydrochloric acid (1 mL) and water (2 mL), heated to 80° C. for 16 h, and then heated to reflux for 3 h. The mixture was concentrated in vacuo to afford the title compound.

c) 4-(2-pyridinyl)benzoyl chloride

Following the procedure of Preparation 1(b), except substituting the compound of Preparation 2(b) for the compound of Preparation 1(a), afforded the title compound.

Preparation 3
Preparation of 4-(2-Thiazolyl)benzoyl Chloride a) ethyl 4-(2-thiazolyl)benzoate Following the general procedure of Preparation 2(a), except substituting 2-thiazolezinc bromide for 4-(ethoxycarbonyl)phenylzinc and ethyl 4-iodobenzoate for 2-bromopyridine, gave the title compound (0.2 g).

b) 4-(2-thiazolyl)benzoic acid

The compound of Preparation 3(a) (0.2 g, 0.86 mmol) was dissolved in methanol (5 mL), treated with concentrated hydrochloric acid (2 mL) and water (8 mL), heated to 80° C. for 16 h, and then heated to reflux for 3 h, concentrated in vacuo, and azeotroped with dichloromethane to give the title compound.

c) 4-(2-thiazolyl)benzoyl chloride

Following the procedure of Preparation 1(b), except substituting the compound of Preparation 3(b) for the compound of Preparation 1(a), afforded the title compound.

Preparation 4
Preparation of 6-Phenyl-3-pyridinecarbonyl Chloride a) 5-methyl-2-(phenyl)pyridine Following the procedure of Preparation 2(a), except substituting 5-methyl-2-pyridinylzinc bromide for 4-(ethoxycarbonyl)phenylzinc iodide and iodobenzene for 2-bromopyridine. afforded the title compound.

b) 6-phenyl-3-pyridinecarboxylic acid

A mixture of the compound of Preparation 4(a) (0.4 g, 2.4 mmol) and water (25 mL) was heated to 90° C. and treated with a solution of potassium permanganate (1.58 g, 10 mmol) in a mixture of water (25 mL) and pyridine (25 ml) added slowly. After the purple color disappeared, additional potassium permanganate (1.58 g) was added and the mixture stirred for 5 h. The hot mixture was filtered, the filter cake was washed with water, and the filtrate was concentrated in vacuo to give a white solid, which was dissolved in water (50 mL) and acidified with 3N hydrochloric acid until no additional precipitate formed. The precipitate was filtered and air-dried to give the title compound. MS(ES) m/e 199.7 [M+H]$^+$.

c) 6-phenyl-3-pyridinecarbonyl chloride

Following the procedure of Preparation 1(b), except substituting the compound of Preparation 4(b) for the compound of Preparation 1(a), gave the title compound.

Preparation 5
Preparation of 4-(4-Pyridinyl)benzoyl Chloride a) 4-(4-pyridinyl)benzoic acid 4-Bromopyridine hydrochloride (0.4 g, 2 mmol), 4-(4,4,5,5-tetramethyl-1,3,2-dioxaborolan-2-yl)benzoic acid (0.5 g, 2 mmol), and tetrakis(triphenylphosphine)palladium(0) (50 mg, 0.04 mmol) in dimethylformamide (15 mL) was treated with 2M potassium carbonate (2 mL) and the mixture was heated to 80° C. for 16 h. The mixture was concentrated in vacuo and the residue was diluted with water to afford a solid which was filtered to afford the title compound (0.26 g).

b) 4-(4-pyridinyl)benzoyl chloride

Using the procedure of Preparation 1(b), except substituting the compound of Preparation 5(a) for the compound of Preparation (1(a), afforded the title compound.

Preparation 6
Preparation of 5-Phenyl-2-pyridinecarbonyl Chloride a) 2-methyl-5-(phenyl)pyridine A solution of 3-(phenyl)pyridine (1.55 g, 10 mmol) in tetrahydrofuran (10 ml) was stirred at −78° C. and treated with methyllithium (1.4 M, 7.5 mL, 10 mmol) in ether. The resulting yellow solution was stirred for 1 h, allowed to warm to 0° C., stirred 1 h, quenched with saturated ammonium chloride, and extracted with ether. The combined organic phase was washed with water and with brine, dried (MgSO4), and concentrated in vacuo. The residue was chromatographed (silica gel, 25% ethyl acetate/hexane) to give the title compound (0.36 g).

b) 5-phenyl-2-pyridinylcarbonyl chloride

Following the general procedure of Preparation 4(b)–(c), except substituting the compound of Preparation 6(a) for the compound of Preparation 4(a), gave the title compound.

Preparation 7
Preparation of 5-phenyl-2-thiophenecarboxylic Acid

Following the procedure of Preparation 1(a), except substituting phenylboronic acid for 4-carboxybenzeneboronic acid and 5-bromo-2-thiophenecarboxylic acid for 3-bromopyridine, afforded the title compound.

Preparation 8
Preparation of N-[1'-(1-Methylethyl)spiro[benzofuran-3 (2H),4'-piperidin]-5-amine a) 5- and 7-nitro-spiro[benzofuran-3(2H),4'-piperidine]

A solution of 1'-methyl-5- and 7-nitro-spiro[benzofuran-3(2H),4'-piperidine] (WO 96/11934) (3 g, 12 mmol) and diisopropylethylamine (2.5 g, 19 mmol) in 1,2-dichloroethane (80 mL) was treated with 1-chloroethyl chloroformate (2.3 g, 16 mmol) at RT, stirred for 1 h, and heated to reflux for 20 min. The mixture was cooled, concentrated in vacuo, and the residue was dissolved in methanol and heated to reflux for 2 h, concentrated in vacuo, and the residue was partitioned between dichloromethane (250 mL) and 5% sodium bicarbonate (50 mL). The organic phase was washed with 5% sodium bicarbonate (50 mL) and the combined aqueous phase was extracted with dichloromethane (2×50 mL). The combined organic phase was dried (Na$_2$SO$_4$) and concentrated to afford the title compound (2.65 g).

b) 1'-(tert-butoxycarbonyl)-5-nitro-spiro[benzofuran-3 (2H),4'-piperidine]

A solution of the compound of Preparation 8(a)(2.65 g, 1.13 mmol) in tetrahydrofuran (300 mL) was treated with di-tert-butyl dicarbonate (2.6 g, 12 mmol) and stirred at RT for 16 h. The mixture was concentrated in vacuo and the residue was crystallized from methanol to afford the title compound (2.1 g).

c) 5-nitro-spiro[benzofuran-3(2H),4'-piperidine]

A solution of the compound of Preparation 8(b)(2.1 g, 6.3 mmol) in dichloromethane (50 mL) and trifluoroacetic acid (10 mL) was kept at RT for 5 h, concentrated in vacuo, and the residue was partitioned between dichloromethane (300 mL) and 5% sodium bicarbonate. The organic phase was washed with 5% sodium bicarbonate and the combined aqueous washes were extracted with dichloromethane. The combined organic phase was dried ($Na_2SO_4$) and concentrated in vacuo to give the title compound (1.45 g): MS(ES) m/e 235.1 [+H]$^+$.

d) 5-nitro-1'-(1-methylethyl)spiro[benzofuran-3(2H),4'-piperidine]

A mixture of the compound of Preparation 8(c) (1.45 g, 6.2 mmol), powdered potassium carbonate (0.86 g, 6.2 mmol) and dimethylformamide (50 mL) containing 2-iodopropane (1.1 g, 6.4 mmol) was stirred and heated to 50° C. for 4 h, treated with 2-iodopropane (0.17 g. 1 mmol) at 50° C. for 90 min, and treated with 2-iodopropane (0.1 g, 1 mmol) at 50° C. for 2 h. The mixture was concentrated in vacuo and the residue was partitioned between ethyl acetate (200 mL) and water (20 mL). The organic phase was washed, dried ($MgSO_4$), concentrated in vacuo, and the residue was chromatographed (silica gel, 5% methanol/dichloromethane) to give the title compound (0.85 g).

e) N-[1'-(1-methylethyl)spiro[benzofuran-3(2H),4'-piperidin]-5-amine

A solution of the compound of Preparation 8(d) (0.78 g, 2.8 mmol) in methanol (250 mL) containing 10% palladium-on-carbon (0.375 g) was shaken in a hydrogen atmosphere (40 psi) for 40 min, filtered, and concentrated in vacuo to afford the title compound (0.6 g).

Preparation 9
Preparation of 4-methyl-2-pyrazinyl-5-thiazolecarbony chloride

Following the procedure of Preparation 1(b), except substituting 4-methyl-2-pyrazinyl-5-thiazolecarboxylic acid for the compound of Preparation 1(a) afforded the title compound.

Example 1
Preparation of N-[3-[2-[Bis(1-methylethyl)amino]ethoxy]-4-methoxyphenyl]-4-(2-thienyl)benzamide A solution of 2-thienylzinc bromide in tetrahydrofuran (0.5M, 5 mL, 2.5 mmol) was added to a solution of N-[3-[2-(diisopropylamino)ethoxy]-4-methoxypheny]-4-iodobenzamide (WO 99/01127) (0.5 g, 1 mmol) in tetrahydrofuran (5 mL) containing tetrakis(triphenylphosphine)palladium(0) (80 mg, 0.06 mmol), and the mixture was stirred at RT for 16 h. The reaction was quenched with saturated ammonium chloride and extracted with ether and dichloromethane. The organic phase was dried ($MgSO_4$), concentrated in vacuo, and chromatographed (silica gel, 5% methanol/dichloromethane) to afford the title compound (0.1 g) MS(ES) m/e 452.8 [M+H]$^+$.

Example 2
Preparation of N-[3-[2-[Bis(1-methylethyl)amino]ethoxy]-4-methoxyphenyl]-4-(3-pyridinyl)benzamide The compound of Preparation 1(b) was dissolved in dichloromethane (5 mL) and treated with 3-[2-(diisopropylamino)ethoxy]-4-methoxyaniline (WO 95/15954) (0.27 g, 1 mmol) followed by diisopropylethylamine (0.14 g, 1 mmol). The mixture was stirred at RT for 16 h, diluted with dichloromethane, extracted twice with 5% sodium carbonate and with water, dried ($MgSO_4$), concentrated in vacuo, and the residue chromatographed (silica gel, 5% methanol/dichloromethane) to give the title compound (20 mg). MS(ES) m/e 448.0 [M+H]$^+$.

Examples 3–7
Preparation of N-[3-[2-[Bis(1-methylethyl)amino]ethoxy]-4-methoxyphenyl]-5-(1-pyrrolyl)-3-pyridinecarboxamide; N-[3-[2-[Bis(1-methylethyl)amino]ethoxy]-4-methoxyphenyl]-4-(2-pyridinyl)benzamide; N-[3-[2-[Bis(1-methylethyl)amino]ethoxy]-4-methoxyphenyl]-4-(2-thiazolyl)benzamide; N-[3-[2-[Bis(1-methylethyl)amino]ethoxy]-4-methoxyphenyl]-6-phenyl-3-pyridinecarboxamide; and N-[3-[2-[Bis(1-methylethyl)amino]ethoxy]-4-methoxyphenyl]-4-(4-pyridinyl)benzamide Following the procedure of Example 2, except substituting the compounds of Preparation 2(c), Preparation 3(c), Preparation 4(c), and Preparation 5(b) for the compound of Preparation 1(b), gave the title compounds:

N-[3-[2-[bis(1-methylethyl)amino]ethoxy]-4-methoxyphenyl]-5-(1-pyrrolyl)-3-pyridinecarboxamide: MS(ES) m/e 437.2 [M+H]$^+$;

N-[3-[2-[bis(1-methylethyl)amino]ethoxy]-4-methoxyphenyl]-4-(2-pyridinyl)benzamideMS(ES) m/e 448.0 [M+H]$^+$;

N-[3-[2-[bis(1-methylethyl)amino]ethoxy]-4-methoxyphenyl]-4-(2-thiazolyl)benzamide: MS(ES) m/e 454.1 [M+H]$^+$;

N-[3-[2-[bis(1-methylethyl)amino]ethoxy]-4-methoxyphenyl]-6-phenyl-3-pyridinecarboxamide: MS(ES) m/e 448.0 [M+H]$^+$; and N-[3-[2-[bis(1-methylethyl)amino]ethoxy]-4-methoxyphenyl]-4-(4-pyridinyl)benzamide: MS(ES) m/e 448.2 [M+H]$^+$.

Example 8
Preparation of N-[3-[2-[Bis(1-methylethyl)amino]ethoxy]-4-methoxyphenyl]-5-phenyl-2-pyridinecarboxamide A solution of the compound of Preparation 6(b) (0.4 g, 2 mmol), 3-[2-(diisopropylamino)]-4-methoxyaniline (WO 95/15954) (0.53 g, 2 mmol), and BOP reagent (0.88 g, 2 mmol) in acetonitrile (30 mL) was treated with triethylamine (0.6 g, 6 mmol), and the mixture was stirred for 16 h. The mixture was diluted with dichloromethane, and extracted with 5% sodium carbonate and with water. The organic phase was dried ($MgSO_4$), concentrated in vacuo, and the residue was chromatographed (silica gel, 5% methanol/dichloromethane) to afford the title compound (0.24 g). MS(ES) m/e 448.2 [M+H]$^+$.

Example 9
Preparation of N-[3-[2-[Bis(1-methylethyl)amino]ethoxyl-4-methoxyphenyl]-3-(2-thienyl)benzamide Following the procedure of Example 1. except substituting N-[3-[2-(diisopropylamino)ethoxy]-4-methoxyphenyl]-3-iodobenzamide (WO 99/01127) for N-[3-[2-(diisopropylamino)ethoxy]-4-methoxyphenyl]-4-iodobenzamide, gave the title compound. MS(ES) m/e 496.7 [M+H]$^+$.

Example 10
Preparation of N-[3-[2-[Bis(1-methylethyl)amino]ethoxy]-4-methoxyphenyl]-5-phenyl-2-thiophenecarboxamide Following the procedure of Example 8, except substituting the compound of Preparation 7 for the compound of Preparation 6(c), gave the title compound. MS(ES) m/e 453.0 [M+H]$^+$.

Example 11
Preparation of N-[3-[2-[Bis(1-methylethyl)amino]ethoxy]-4-methoxyphenyl]-2-thiophenecarboxamide a) 3-[2-[bis(1-methylethyl)amino]ethoxy]-4-methoxyaniline]-/(4-formyl-3,5-dimethoxyphenoxy)-Merrifield resin adduct A mixture of 4-formyl-3,5-dimethoxyphenoxy-Merrifield resin (Boojamra et al., *J. Org. Chem.* 1995, 60, 5742), 3-[2-(diisopropylamino)ethoxy]-4-methoxyaniline (WO 95/15954), and sodium triacetoxyborohydride in dimethylformamide containing 1% acetic acid was shaken to afford the title adduct.

b) N-[3-[2-[bis(1-methylethyl)amino]ethoxy]-4-methoxyphenyl]-2-thiophenecarboxamide/(4-formyl-3,5-dimethoxyphenoxy)-Merrifield resin adduct The resin of Example 11(a) in dimethylformamide was treated with pyridine (10 equivalents) and with a mixture of 10 equivalents each of 2-thiophenecarboxylic acid, N-bromosuccinimide and triphenylphosphine. The resin was washed to afford the title adduct.

c) N-[3-[2-[bis(1-methylethyl)amino]ethoxy]-4methoxyphenyl]-2-thiophenecarboxamide The resin of Example 11(b) was stirred in a mixture of trifluoroacetic acid:dichloromethane:water (50:48:2), filtered, and the filtrate concentrated in vacuo to afford the title compound. MS(ES) m/e 377.0 [M+H]$^+$.

Examples 12–14

Following the procedure of Example 11(b)–11(c), except substituting 3-pyridinecarboxylic acid, 6-chloro-3-pyridinecarboxylic acid, and 5-bromo-3-pyridinecarboxylic acid for 2-thiophenecarboxylic acid, afforded the title compounds:

N-[3-[2-[bis(1-methylethyl)amino]ethoxy]-4-methoxyphenyl]-3-pyridinecarboxamide: MS(ES) m/e 372.0 [M+H]$^+$;

6-chloro-N-[3-[2-[bis(1-methylethyl)amino]ethoxy]-4-methoxyphenyl]-3-pyridinecarboxamide: MS(ES) m/e 406.0 [M+H]$^+$; and 5-bromo-N-[3-[2-[bis(1-methylethyl)amino]ethoxy]-4-methoxyphenyl]-3-pyridinecarboxamide: MS(ES) m/e 450.0 [M+H]$^+$.

Example 15

Preparation of N-[3-[2-(diethylamino)ethoxy]-4-methoxyphenyl]2-thiophenecarboxamide Following the procedure of Example 11, except substituting 3-(2-diethylamino)ethoxy-4-methoxyaniline (WO 96/23769) for 3-[2-(diisopropylamino)ethoxy]-4-methoxyaniline, afforded the title compound. MS(ES) m/e 349.0 [M+H]$^+$.

Example 16

Preparation of N-[1'-Isopronyl-spiro[benzofuran-3(2H),4'-piperidin]-5-yl)-2-(2,3-dihydro-1,4-benzodioxan-2-yl )-4-thiazolecarboxamide Following the procedure of Example 8, except substituting 2-(2,3-dihydro-1,4-benzodioxin-2-yl)-4-thiazolecarboxylic acid for the compound of Preparation 6(b) and the compound of Preparation 8(e) for 3-[2-(diisopropylamino)ethoxy]4-methoxyaniline, gave the title compound). MS(ES) m/e 492.0 [M+H]$^+$.

Example 17

Preparation of N-[3-[2-[Bis(1-methylethyl)amino]ethoxy]-4-methoxyphenyl]-2-(2,3-dihydro-1,4-benzodioxin-2-yl)-4-thiazolecarboxamide Following the procedure of Example 2, except substituting 2-(1,4-benzodioxan-2-yl)thiazole-4-carbonyl chloride for the compound of Preparation 1(b), gave the title compound. MS(ES) m/e 512.1 [M+H]$^+$.

Examples 18–19

Preparation of (+)-N-[3-[2-[Bis(1-methylethyl)amino]ethoxy]-4-methoxyphenyl]-2-(2,3-dihydro-1,4-benzodioxin-2-yl)-4-thiazolecarboxamide and (−)-N-[3-[2-[Bis(1 -methylethyl)amino]ethoxy]-4-methoxyphenyl]-2-(2,3-dihydro-1,4-benzodioxin-2-yl)-4-thiazolecarboxamide The compound of Example 17 was resolved by HPLC (Chiralcel OJ, 21.2×250 mm, 15 mL/min, 0.1:99.9 diethylamine/methanol, UV detection at 254 nm) to afford the title compounds:

(+)-N-[3-[2-[bis(1-methylethyl)amino]ethoxy]-4-methoxyphenyl]-2-(2,3-dihydro-1,4-benzodioxin-2-yl)-4-thiazolecarboxamide: MS(ES) m/e 512.0 [M+H]$^+$; [•]$_D$=10.4°; and (−)-N-[3-[2-[bis(1-methylethyl)amino]ethoxy]-4-methoxyphenyl]-2-(2,3-dihydro-1,4-benzodioxin-2-yl)-4-thiazolecarboxamide: MS(ES) m/e 512.0 [M+H]$^+$; [•]$_D$=−10.2°.

Example 20

Preparation of N-[3-[2-[Bis(1-methylethyl)amino]ethoxy]4-methoxyphenyl]4-methyl-2-pyrazinyl-5-thiazolecarboxamide Following the procedure of Example 2, except substituting the compound of Preparation 9 for the compound of Preparation 1(b) afforded: the title compound. mp 105–106° C.

Examples 21–22

Preparation of N-[3-[2-[Bis(1-methylethyl)amino]ethoxy]-4-methoxyphenyl]-5-chloro-1H-indole-2-carboxamide and N-[3-[2-[Bis(1-methylethyl)amino]ethoxy]-4-methoxyphenyl]-5-chloro-2-benzofurancarboxamide Following the procedure of Example 8, except substituting 5-chloro-1H-indole-2-carboxylic acid and 5-chloro-2-benzofurancarboxylic acid for the compound of Preparation 6(b) and purifying the residues obtained by HPLC (ODS-A, 20×50 mm, A:acetonitrile B:water-0.1% trifluoroacetic acid, 10–90% during 10 min. UV detection at 254 nm) afforded the title compounds:

N-[3-[2-[bis(1-methylethyl)amino]ethoxy]-4-methoxyphenyl]-5-chloro-1H-indole-2-carboxamide: MS(ES) m/e 443.7 [M+H]$^+$; and N-[3-[2-[bis(1-methylethyl)amino]ethoxy]-4-methoxyphenyl]-5-chloro-2-benzofurancarboxamide: MS(ES) m/e 445.1 [M+H]$^+$.

Example 23

Preparation of N-[3-[2-(Diethylamino)ethoxy]-4-methoxyphenyl]-2-(2,3-dihydro-1,4-benzodioxin-2-yl)-4-thiazolecarboxamide Following the general procedure of Example 11(b)–(c), the resin of Example 11(a) in dichloromethane was treated with 2-(2,3-dihydro-1,4-benzodioxin-2-yl)-4-thiazolecarbonyl chloride. DMAP, and pyridine. The resin was washed and treated with a mixture of trifluoroacetic acid:dichloromethane:water to afford the title compound. MS(ES) m/e 484.0 [M+H]$^+$.

Examples 24–26

Following the procedure of Example 23, except using 3-[2-(diethylamino)ethoxy]-4-methoxyaniline, 3-[2-(dimethylamino)ethoxy]-4-methoxyaniline and 3-[2-[bis(1-methylethyl)amino]ethoxy]-4-methoxyaniline and using 5-methyl-2-phenyl-2H-1,2,3-triazole-4-carboxyl chloride and 2-(2,3-dihydro-1,4-benzodioxin-2-yl)4-thiazolecarbonyl chloride, afforded the title compounds:

N-[3-[2-[bis(1-methylethyl)amino]ethoxy]-4-methoxyphenyl]-5-methyl-2-phenyl-2H-1,2,3-triazole-4-carboxamide: MS(ES) m/e 452.2 [M+H]$^+$;

N-[3-[2-(diethylamino)ethoxy]-4-methoxyphenyl]-5-methyl-2-phenyl-2H-1,2,3-triazole-4-carboxamide: MS(ES) m/e 424.0 [M+H]+; and N-[3-[2-(dimethylamino)ethoxy]-4-methoxyphenyl]-2-(2,3-dihydro-1,4-benzodioxin-2-yl)-4-thiazolecarboxamide: MS(ES) m/e 456.0 [M+H]+.

Examples 27–55

Following the procedure of Example 11(a)–(c), except using 3-[2-(diethylamino)ethoxy]-4-methoxyaniline and 3-[2-[bis(1-methylethyl)amino]ethoxy]-4-methoxyaniline and substituting 4-methyl-2-[4-(trifluoromethyl)phenyl]-5-thiazolecarboxylic acid, 2-(3-bromo-2-thienyl)-4-thiazolecarboxylic acid, 2-(2,3-dihydro-1,4-benzodioxin-2-yl)-4-methyl-5-thiazolecarboxylic acid, 2-phenyl-4-thiazolecarboxylic acid, 4-methyl-2-phenyl-5-thiazolecarboxylic acid, 4-methyl-2-(4-chlorophenyl)-5-thiazolecarboxylic acid, 4-methyl-2-[3-(trifluoromethyl)phenyl]-5-thiazolecarboxylic acid, 2-[2-chloro-4-(trifluoromethyl)phenyl]-4-thiazolecarboxylic acid, 2-(2,3-dichlorophenyl)-4-thiazolecarboxylic acid, 2-[3-(trifluoromethyl)phenyl]-4-thiazolecarboxylic acid, and 4-methyl-2-(4-chlorophenyl)-5-thiazolecarboxylic acid for 2-thiophenecarboxylic acid, afforded the title compounds:

N-[3-[2-[bis(1-methylethyl)amino]ethoxy]-4-methoxyphenyl]-4-methyl-2-[4-(trifluoromethyl)phenyl]-5-thiazolecarboxamide: MS(ES) m/e 536.2 [M+H]+;

N-[3-[2-[bis(1-methylethyl)amino]ethoxy]-4-methoxyphenyl]-2-(3-bromo-2-thienyl)-4-thiazolecarboxamide: MS(ES) m/e 538.1 [M+H]+;

N-[3-[2-(diethylamino)ethoxy]-4-methoxyphenyl]-2-(3-bromo-2-thienyl)-4-thiazolecarboxamide: MS(ES) m/e 510.0 [M+H]+;

N-[3-[2-[bis(1-methylethyl)amino]ethoxy]phenyl]-2-(3-bromo-2-thienyl)-4-thiazolecarboxamide: MS(ES) m/e 508.1 [M+H]+;

N-[3-[2-[bis(1-methylethyl)amino]ethoxy]-4-methoxyphenyl]-2-(2,3-dihydro-1,4-benzodioxin-2-yl)-4-methyl-5-thiazolecarboxamide: MS(ES) m/e 526.2 [M+H]+;

N-[3-[2-(diethylamino]ethoxy)-4-methoxyphenyl]-2-(2,3-dihydro-1,4-benzodioxin-2-yl)-4-methyl-5-thiazolecarboxamide: MS(ES) m/e 498.2 [M+H]+;

N-[3-[2-[bis(1-methylethyl)amino]ethoxy]phenyl]-2-(2,3-dihydro-1,4-benzodioxin-2-yl)-4-methyl-5-thiazolecarboxamide: MS(ES) m/e 496.0 [M+H]+;

N-[3-[2-[bis(1-methylethyl)amino]ethoxy]-4-methoxyphenyl]-2-phenyl-4-thiazolecarboxamide: MS(ES) m/e 454.2 [M+H]+;

N-[3-[2-(diethylamino)ethoxy]4-methoxyphenyl]-2-phenyl-4-thiazolecarboxamide: MS(ES) m/e 426.0 [M+H]+;

N-[3-[2-[bis(1-methylethyl)amino]ethoxy]phenyl]-2-phenyl-4-thiazolecarboxamide: MS(ES) m/e 424.0 [M+H]+;

N-[3-[2-[bis(1-methylethyl)amino]ethoxy]-4-methoxyphenyl]-4-methyl-2-phenyl-5-thiazolecarboxamide: MS(ES) m/e 468.2 [M+H]+;

N-[3-[2-(diethylamino)ethoxy]-4-methoxyphenyl]-4-methyl-2-phenyl-5-thiazolecarboxamide: MS(ES) m/e 440.2 [M+H]+;

N-[3-[2-[bis(1-methylethyl)amino]ethoxy]phenyl]4-methyl-2-(4-chlorophenyl)-5-thiazolecarboxamide: MS(ES) m/e 472.2 [M+H]+;

N-[3-[2-[bis(1-methylethyl)amino]ethoxy]4-methoxyphenyl]-2-(4-chlorophenyl)-5-thiazolecarboxamide: MS(ES) m/e 488.2 [M+H]+;

N-[3-[2-(diethylamino)ethoxy]-4-methoxyphenyl]-2-(4-chlorophenyl)-5-thiazolecarboxamide: MS(ES) m/e 460.0 [M+H]+;

N-[3-[2-[bis(1-methylethyl)amino]ethoxy]4-methoxyphenyl]-4-methyl-2-[3-(trifluoromethyl)phenyl]-5-thiazolecarboxamide: MS(ES) m/e 536.2 [M+H]+;

N-[3-[2-(diethylamino)ethoxy]4-methoxyphenyl]-4-methyl-2-[3-(trifluoromethyl)phenyl]-5-thiazolecarboxamide: MS(ES) m/e 508.2 [M+H]+;

N-[3-[2-[bis(1-methylethyl)amino]ethoxy]phenyl]-4-methyl-2-[3-(trifluoromethyl)phenyl]-5-thiazolecarboxamide: MS(ES) m/e 506.2 [M+H]+;

N-[3-[2-[bis(1-methylethyl)amino]ethoxy]-4-methoxyphenyl]-2-[2-chloro-4-(trifluoromethyl)phenyl]-4-thiazolecarboxamide: MS(ES) m/e 556.2 [M+H]+;

N-[3-[2-(diethylamino)ethoxy]4-methoxyphenyl]-2-[2-chloro-4-(trifluoromethyl)phenyl]-4-thiazolecarboxamide: MS(ES) m/e 528.0 [M+H]+;

N-[3-[2-[bis(1-methylethyl)amino]ethoxy]phenyl]-2-[2-chloro4-(trifluoromethyl)phenyl]-4-thiazolecarboxamide: MS(ES) m/e 526.2 [M+H]+;

N-[3-[2-[bis(1-methylethyl)amino]ethoxy]4-methoxyphenyl]-2-(2,3-dichlorophenyl)-4-thiazolecarboxamide: MS(ES) m/e 522.1 [M+H]+;

N-[3-[2-(diethylamino)ethoxy]-4-methoxyphenyl]-2-(2,3-dichlorophenyl)-4-thiazolecarboxamide: MS(ES) m/e 494.1 [M+H]+;

N-[3-[2-[bis(1-methylethyl)amino]ethoxy]phenyl]-2-(2,3-dichlorophenyl)4-thiazolecarboxamide: MS(ES) m/e 492.1 [M+H]+;

N-[3-[2-[bis(1-methylethyl)amino]ethoxy]4-methoxyphenyl]-2-[3-(trifluoromethyl)phenyl]-4thiazolecarboxamide: MS(ES) m/e 522.2 [M+H]+;

N-[3-[2-(diethylamino)ethoxy]-4-methoxyphenyl]-2-[3-(trifluoromethyl)phenyl]-4-thiazolecarboxamide: MS(ES) m/e 494.2 [M+H]+;

N-[3-[2-[bis(1-methylethyl)amino]ethoxy]phenyl]-2-[3-(trifluoromethyl)phenyl]-4-thiazolecarboxamide: MS(ES) m/e 492.2 [M+H]+;

N-[3-[2-(diethylamino)ethoxy]-4-methoxyphenyl]-4-methyl-2-[4-(trifluoromethyl)phenyl]-5-thiazolecarboxamide: MS(ES) m/e 508.2 [M+H]+; and N-[3-[2-[bis(1-methylethyl)amino]ethoxy]-4-methoxyphenyl]-4-methyl-2-(4-chlorophenyl)-5-thiazolecarboxamide: MS(ES) m/e 502.2 [M+H]+.

Examples 56–60

Following the procedure of Example 11(a)–(c), except using 3-[2-[bis(1-methylethyl)amino]ethoxy]4-methoxyaniline, 3-[3-[bis(1-methylethyl)amino]propyl]-4-methoxyaniline and 3-[3-[bis(1-methylethyl)amino]propoxy]-4-methoxyaniline and substituting 3-chloro-benzo[b]thiophene-2-carboxylic acid and 6-chloro-2H-1-benzopyran-3-carboxylic acid for 2-thiophenecarboxylic acid, afforded the title compounds:

N-[3-[2-[bis(1-methylethyl)amino]ethoxy]-4-methoxyphenyl]-3-chloro-benzo[b]thiophene-2-carboxamide: MS(ES) m/e 461.0 [M+H]+;

N-[3-[3-[bis(1-methylethyl)amino]propyl]4-methoxyphenyl]-3-chloro-benzo[b]thiophene-2-carboxamide: MS(ES) m/e 459.2 [M+H]+;

N-[3-[3-[bis(1-methylethyl)amino]propoxy]-4-methoxyphenyl]-3-chloro-benzo[b]thiophene-2-carboxamide: MS(ES) m/e 475.0 [M+H]+;

N-[3-[3-[bis(1-methylethyl)amino]propyl]-4-methoxyphenyl]-6-chloro-2H-1-benzopyran-3-carboxamide: MS(ES) m/e 457.2 [M+H]+; and N-[3-[3-[bis(1-methylethyl)amino]propoxy]-4-methoxyphenyl]-6-chloro-2H-1-benzopyran-3-carboxamide: MS(ES) m/e 473.2 [M+H]+.

Example 61
Preparation of N-[3-[2-[bis(1-methylethyl)amino]ethoxy]-4-methoxyphenyl]-6-chloro-2H-1-benzopyran-3-carboxamide Following the procedure of Example 8, except substituting 6-chloro-2H-1-benzopyran-3-carboxylic acid for the compound of Example 6(b) afforded the title compound. MS(ES) m/e [M+H]$^+$.

Biological Data

CCR5 Receptor Binding Assay

CHO cell membranes (0.25×10$^6$ cell equivalents) derived from CHO cells stably transfected with CCR5 were incubated with 0.3 $^{125}$I-RANTES in a 96 well plate for 45 min at room temperature (final reaction volume 200 ul). The reaction was terminated by filtration and the filters (GF/C) were washed twelve times with a solution of phosphate buffered saline containing 0.1% bovine serum albumin and 0.05% NaN$_3$. The radioactivity bound to filters was measured by liquid scintillation spectrometry. Non-specific binding was determined in the presence of unlabelled RANTES (10 or 30 nM) and averages 30–50% of total binding.

CCR5 Receptor Functional Assay

The cellular functional assay used to assess antagonist activity of compounds was RANTES-induced Ca$^{2+}$ mobilization in RBL 2H3 cells stably expressing the hCCR5 receptor (RBL 2H3 hCCR5). Agonist activity is determined by Ca$^{2+}$ mobilization in the same cells which is inhibitable by a selective CCR5 antagonist. Cells were grown to 80–100% confluency in T-150 flasks and washed with phosphate-buffered saline. Cells were lifted from the flasks by treating with 3 mL of 1 mM EDTA for 3 min at room temperature and diluting to 2×10$^6$ cells/mL with Krebs Ringer Henseleit buffer (KRH; 118 mM NaCl, 4.6 mM KCl. 25 mM NaHCO$_3$, 1 mM KH$_2$PO$_4$ and 11 mM glucose) containing 5 mM HEPES (pH 7.4). 1 mM CaCl$_2$, 1 mM MgCl$_2$ and 0.1% BSA and centrifuged at 200 g for 3 min. Cells were resuspended at 2×10$^6$ cells/mL in the same buffer with 2 $\mu$M Fura-2AM, and incubated for 35 min at 37° C. Cells were centrifuged at 200×g for 3 min and resuspended in the same buffer without Fura-2AM, then incubated for 15 min at 37° C. to complete the hydrolysis of intracellular Fura-2AM, and then centrifuged as before. Cells (10$^6$ cells/mL) were resuspended in cold KRH with 5 mM HEPES (pH 7.4), 1 mM CaCl$_2$, 1 mM MgCl$_2$ and 0.1% gelatin and maintained on ice until assayed. For antagonist studies, aliquots (2 mL) of cells were prewarmed at 37° C. for 5 min in 3 mL plastic cuvettes and fluorescence measured in a fluorometer (Johnson Foundation Biomedical Group, Philadelphia. Pa. USA) with magnetic stirring and temperature maintained at 37° C. Excitation was set at 340 nm and emission set at 510 nm. Various concentrations of antagonists or vehicle were added and fluorescence monitored for ~15 sec to ensure that there was no change in baseline fluorescence, followed by the addition of 33 nM RANTES. Maximal Ca$^{2+}$ attained after 33 nM RANTES stimulation was calculated as described by Grynkiewicz et al., (1985). The percent of maximal RANTES-induced Ca$^{2+}$ was determined for each concentration of antagonist and the IC$_{50}$, defined as the concentration of test compound that inhibits 50% of the maximal 33 nM RANTES response. obtained from the concentration-response curves (5–7 concentrations of antagonists).

The compounds of this invention show CCR5 receptor modulator activity having IC$_{50}$ values in the range of 0.0001 to 100 $\mu$M. The full structure/activity relationship has not yet been established for the compounds of this invention. However, given the disclosure herein, one of ordinary skill in the art can utilize the present assays in order to determine which compounds of this invention are modulators of the CCR5 receptor and which bind thereto with an IC$_{50}$ value in the range of 0.0001 to 100 $\mu$M.

All publications. including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way.

The embodiments of the invention in which an exclusive property or privilege is claimed are defined as follows.

What is claimed is:

1. A method of treating a CCR5-mediated disease state in mammals which comprises administering to a mammal in need of such treatment, an effective amount of a compound which is N-[3-[2-[Bis(1-methylethyl)amino]ethoxy]-4-methoxyphenyl]-6-chloro-2H-1-benzopyran-3-carboxamide or a pharmaceutically acceptable salt thereof.

2. The method of claim 1, wherein the CCR5-mediated disease state is an inflammatory disease.

3. The method of claim 1, wherein the CCR5-mediated disease state is an atopic disorder.

4. The method of claim 1, wherein the CCR5-mediated disease state is an autoimmune disorder.

5. A compound which is N-[3-[2-[Bis(1-methylethyl)amino]ethoxy]-4-methoxyphenyl]-6-chloro-2H-1-benzopyran-3-carboxamide.

* * * * *